US010287542B2

(12) United States Patent
Park et al.

(10) Patent No.: US 10,287,542 B2
(45) Date of Patent: May 14, 2019

(54) APPARATUS FOR AUTOMATICALLY PREPARING CELL-FREE PROTEINS AND METHOD FOR PREPARING PROTEINS USING SAME

(71) Applicant: BIONEER CORPORATION, Daejeon (KR)

(72) Inventors: Han Oh Park, Daejeon (KR); Jong Kab Kim, Daejeon (KR); Ji Won Han, Daejeon (KR); You Sang Cho, Daejeon (KR); Min Jung Kim, Daejeon (KR); Ha Neul Kim, Daejon (KR); Yang Won Lee, Daejeon (KR); Nam Il Kim, Daejeon (KR)

(73) Assignee: BIONEER CORPORATION, Daejeon (KR)

( * ) Notice: Subject to any disclaimer, the term of this patent is extended or adjusted under 35 U.S.C. 154(b) by 103 days.

(21) Appl. No.: 14/648,891

(22) PCT Filed: Nov. 29, 2013

(86) PCT No.: PCT/KR2013/011022
§ 371 (c)(1),
(2) Date: Jun. 1, 2015

(87) PCT Pub. No.: WO2014/084672
PCT Pub. Date: Jun. 5, 2014

(65) Prior Publication Data
US 2015/0299637 A1    Oct. 22, 2015

(30) Foreign Application Priority Data

Nov. 30, 2012 (KR) .................. 10-2012-0138335
Feb. 28, 2013 (KR) .................. 10-2013-0022324

(51) Int. Cl.
| C07K 1/14 | (2006.01) |
| C12M 1/00 | (2006.01) |
| C12M 1/24 | (2006.01) |
| C12M 1/32 | (2006.01) |
| C12M 1/26 | (2006.01) |
| C12M 1/34 | (2006.01) |
| C12P 21/00 | (2006.01) |
| C07K 1/02 | (2006.01) |
| C07K 1/04 | (2006.01) |
| C07K 1/22 | (2006.01) |
| C07K 1/36 | (2006.01) |

(52) U.S. Cl.
CPC ............ C12M 29/04 (2013.01); C07K 1/02 (2013.01); C07K 1/047 (2013.01); C12M 23/08 (2013.01); C12M 23/12 (2013.01); C12M 23/38 (2013.01); C12M 29/00 (2013.01); C12M 33/04 (2013.01); C12M 41/12 (2013.01); C12M 47/12 (2013.01); C12P 21/00 (2013.01); C07K 1/22 (2013.01); C07K 1/36 (2013.01)

(58) Field of Classification Search
CPC ........ A61K 38/00; A61K 39/00; C07K 14/21; C07K 16/461; C07K 2319/00; C07K 1/02; C07K 1/047; C07K 1/22; C07K 1/36; A61M 1/3693; B04B 13/00; B04B 2013/006; C12M 23/08; C12M 23/12; C12M 23/38; C12M 29/00; C12M 29/04; C12M 33/04; C12M 41/12; C12M 47/12; C12P 21/00; G01N 15/042; G01N 15/05; G01N 2015/047
See application file for complete search history.

(56) References Cited

U.S. PATENT DOCUMENTS

| 6,927,025 B1 | 8/2005 | Carr et al. |
| 7,118,883 B2 | 10/2006 | Inoue et al. |
| 2004/0115760 A1 | 6/2004 | Metzler et al. |
| 2006/0257997 A1 | 11/2006 | Endo et al. |
| 2011/0009608 A1 | 1/2011 | Kim et al. |

FOREIGN PATENT DOCUMENTS

| CN | 1449449 A | 10/2003 |
| CN | 101434902 A | 5/2009 |
| CN | 101990639 A | 3/2011 |
| EP | 1143009 A1 | 10/2001 |
| EP | 1479776 A1 | 11/2004 |

(Continued)

OTHER PUBLICATIONS

Office Action dated Jan. 12, 2016 of corresponding Japanese Patent Application No. 2015-532983—4 pages.
International Search Report dated Mar. 11, 2014 of PCT/KR2013/011022 which is the parent application and its English translation—4 pages.
Office Action dated Mar. 17, 2016 of corresponding Chinese Patent Application No. 201380069009.1 and its English translation—18 pages.

(Continued)

*Primary Examiner* — Lisa J Hobbs
(74) *Attorney, Agent, or Firm* — Hultquist, PLLC; Steven J. Hultquist

(57) ABSTRACT

An automated cell-free protein production system comprises: a protein expression reaction unit comprising a reaction vessel that includes a plurality of dialysis tubes, each including a dialysis membrane and being open at its top; a reaction temperature control unit configured to heat or cool the reaction vessel; a pipette array comprising a plurality of pipettes and configured to suck or discharge solutions using the pipettes; a pipette array moving unit configured to move the pipette array in an upward and downward direction, a forward and backward direction or a left and right direction so as to move solutions; a protein purification unit including a magnetic field application device; and a multi-well plate mounting unit having mounted therein a multi-well plate kit configured to supply solutions that are used for protein production.

20 Claims, 9 Drawing Sheets

(56) References Cited

FOREIGN PATENT DOCUMENTS

| EP | 2749567 A2 | 7/2014 |
|---|---|---|
| JP | 2003-502146 A | 1/2003 |
| JP | 2006-129702 A | 5/2006 |
| JP | 2011-516075 A | 5/2011 |
| KR | 10-0385298 B1 | 5/2003 |
| KR | 10-0534558 B1 | 12/2005 |
| KR | 10-2006-0008294 A | 1/2006 |
| KR | 10-0733712 B1 | 6/2007 |
| KR | 10-1025135 B1 | 3/2011 |
| KR | 10-2011-0121588 A | 11/2011 |
| KR | 10-2013-0023091 A | 3/2013 |
| RU | 2340627 C2 | 12/2008 |
| WO | 2011/136624 A2 | 11/2011 |

OTHER PUBLICATIONS

Kim et al., "Cell-free synthesis and in situ isolation of recombinant proteins", Protein Expression and Purification, 2006, vol. 45, pp. 249-254.

Lee et al., "Ribosomal synthesis and in situ isolation of peptide molecules in cell-free translation system", Protein Expression and Purification, 2010, vol. 71, pp. 16-20.

Office Action dated Jun. 22, 2015 of corresponding Korean Patent Application No. 10-2013-0022324—5 pages.

Bardoczy et al, "A set of ligation-independent in vitro translation vectors for eukaryotic protein production", BMC Biotechnology, Mar. 27, 2008, vol. 8, No. 32, in 7 pages.

"Fully automatic protein synthesis and nucleic acid extracted system ExiProgen", The Korean Society for Microbiology and Biotechnology, Nov. 24, 2011, vol. 24, No. 10, and a summary translation in English, in 7 pages.

Aoki et al., "Automated system for high-throughput protein production using the dialysis cell-free method", Protein Expression and Purification, Dec. 1, 2009, vol. 68, pp. 128-136.

Sawasaki et al., "A cell-free protein synthesis system for high-throughput proteomics", Proceedings of the National Academy of Sciences, Nov. 12, 2002, vol. 99, No. 23, pp. 14652-14657.

Office Action dated Jun. 17, 2016 of corresponding Russian Patent Application No. 2015125725—15 pages.

Supplementary European Search Report dated Jun. 24, 2016 of corresponding European Patent Application No. 13858370.3—10 pages.

Spirin, A., Ed., et al, "Cell-Free Protein Synthesis: Practical Advice for Beginners and Experts Alike", "Cell-Free Protein Synthesis", 2008, pp. 103, Figure 6.3B, Publisher: Sigma-Aldrich.

Au, L., At Al., "Gene Synthesis by a LCR-Based Approach: High-Level Production of Leptin-L54 Using Synthetic Gene in *Escherichia coli*", "Biochemical and Biophysical Research Communications", 1998, pp. 200-203, vol. 248, No. 1, Publisher: Academic Press.

Bioneer Corporation, "ExiProgen TM EC-TagfreeProtein Synthesis Kit: User's Guide", May 2013, pp. 1-60, vol. 1.0.

Kim, D., et al., "A Semicontinuous Prokaryotic Coupled Transcription/Translation System Using a Dialysis Membrane", "Biotechnol. Prog.", 1996, pp. 645-649, vol. 12, No. 5, Publisher: American Chemical Society and American Institute of Chemical Engineers.

Lee, C., et al., "Development of high-throughput protein production technology", "Ministry of Science and Technology", 2005, pp. 17-30.

FIG. 8
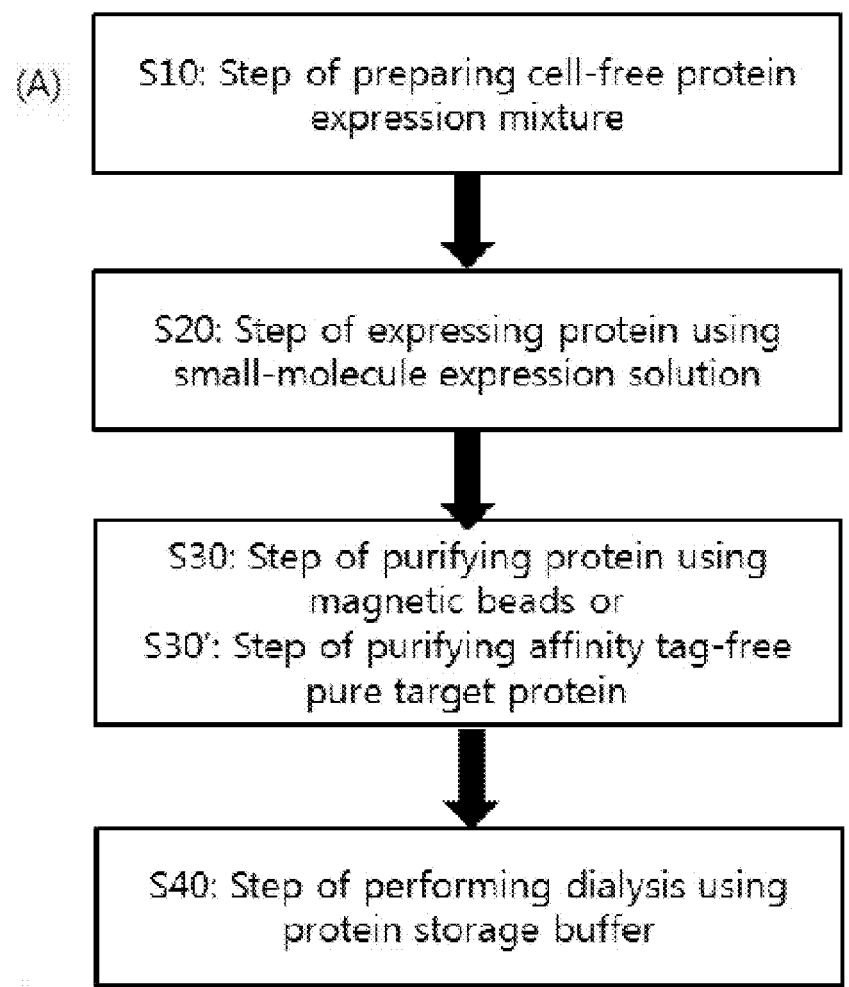
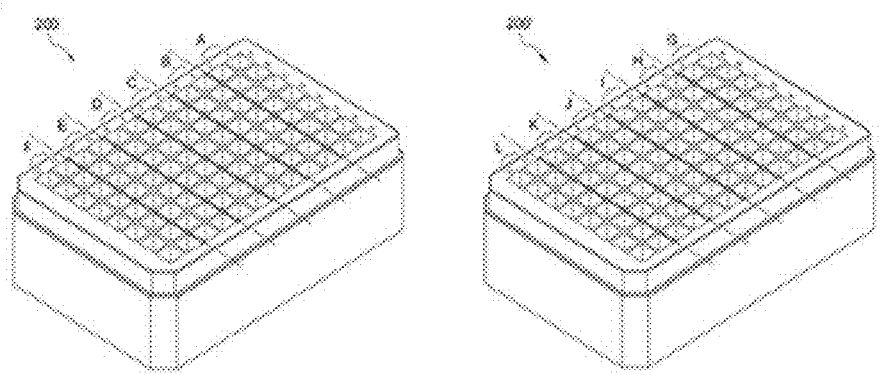

APPARATUS FOR AUTOMATICALLY PREPARING CELL-FREE PROTEINS AND METHOD FOR PREPARING PROTEINS USING SAME

TECHNICAL FIELD

The present invention relates to an automated cell-free protein production system and a method for producing a protein using the same. More specifically, the present invention relates to an automated cell-free protein production system comprising: a protein expression reaction unit comprising a reaction vessel that includes a plurality of dialysis tubes, each including a dialysis membrane and being open at its top; a reaction temperature control unit configured to heat or cool the reaction vessel; a pipette array comprising a plurality of pipettes and configured to suck or discharge solutions using the pipettes; a pipette array moving unit configured to move the pipette array in an upward and downward direction, a forward and backward direction or a left and right direction so as to move solutions; a protein purification unit including a magnetic field application device; and a multi-well plate mounting unit having mounted therein a multi-well plate kit configured to supply solutions that are used for protein production, and a method for producing a protein using the same.

Also, more specifically, the present invention relates to an automated protein production system and method, which can synthesize an affinity tag-free pure target protein in addition to an affinity-tagged target protein, and can automatically and rapidly replace an eluate solution containing a finally purified protein with a desired protein storage buffer by multi-step dialysis, and thus can automatically and conveniently produce a plurality of proteins in large amounts.

Moreover, the present invention relates to a reaction kit for automated cell-free protein production, which comprises a multi-well plate kit for storing a solution required for protein production, and a dialysis tube including a dialysis membrane.

BACKGROUND ART

Generally, methods of producing recombinant proteins are performed using various cell lines such as *E. coli*, yeast and animal cells are used. These methods comprise transforming a recombinant protein expression vector into a cell line, culturing the cell line to express the target protein, and lysing the cells to purify the target protein.

These methods require a process for selecting a strain for stably expressing the recombinant protein, and then a series of processes, including cell culture, cell disruption and protein purification, should be performed. Thus, these methods require large amounts of time and effort.

In addition, cytotoxic proteins or membrane proteins are difficult to express. Thus, in the case of these proteins, many efforts are required, such as attempting various expression conditions. For this reason, there is a problem in that a time from several days to several months is required for production of a single protein.

In order to overcome this problem, there have been developed cell-free protein expression methods for expressing a protein in a reaction vessel such as a test tube within a short time without using cells, and products associated therewith. These methods are intended to express a desire protein without cell culture. These methods use a vector comprising a target gene, a cell extract obtained by isolation/purification after cell culture, and a protein expression solution including amino acids, triphosphate ribonucleic acid, and an energy source and a buffer. In these methods, a gene encoding a desired protein is transcribed into mRNA by RNA polymerase contained in a cell extract, and the mRNA is translated to the protein using the ribosome, tRNA and the like contained in the cell extract.

The cell-free protein expression method was commercialized by Roche, Promega and the like. In this method, a template DNA (e.g., expression vector, PCR product, etc.) capable of expressing protein, a cell lysate, and an expression solution including amino acid, triphosphate ribonucleic acid and an energy source, are added to a test tube, and then allowed to react at a suitable temperature (30 to 40° C.) for a suitable time (1-3 hours) to express the target protein. This method is advantageous over a method of expressing a protein using cells, in that a significantly reduced amount of time is required, and cytotoxic proteins or membrane proteins can be expressed.

In addition, systems capable of producing proteins in a convenient manner by automatically performing cell-free protein expression were developed.

Such systems include RTS (Rapid Translation System) developed by Roche. The RTS can perform cell-free protein expression with high efficiency. In this system, a dialysis membrane is disposed in the bottom of a reaction vessel in order to prevent a reaction from being stopped due to energy source exhaustion and the accumulation of a protein synthesis inhibitor such as phosphoric acid during the progression of cell-free protein expression. For dialysis, this reaction vessel is placed in an at least 10-fold volume of a vessel containing a small-molecule expression solution in order to maximize the reaction. As described in Kim, D.-M. and Choi, C.-Y., *Biotechnol. Prog.*, 12(5):645, 1996, this principle is based on the principle according to which the expression level of a protein can be increased up to 10 times by continuously replacing a small-molecule expression solution containing triphosphate ribonucleic acid, an amino acid and an energy source through a dialysis membrane.

However, this method has a problem in that, a small-molecule expression solution having a volume corresponding to at least 10 times the volume of an expression solution should also be used, the overall size of the reaction vessel becomes greater, and thus the size of the system significantly increases when various kinds of proteins are to be simultaneously synthesized in parallel. In addition, the system is not automated, and can perform only a function of stirring a reaction solution at a certain temperature. Thus, a separate process such as the purification of a synthesized protein after the reaction should be performed.

The RIKEN institute (Japan) automated protein expression by constructing this large-scale system, although the detailed structure of the system was not explained (Alexander Spirin & James R. Swartz, Cell-Free Protein Synthesis, p 103, FIG. 6.3B). Yaeta Endo et al. developed a cell-free method of expressing a protein using a wheat germ extract, and developed an automated system based on a principle different from the RTS system. Also, Yaeta Endo et al. could increase the protein expression yield by diluting a cell-free protein expression solution with a small-molecule expression solution and concentrating the dilution (US 2006/0257997 A1).

However, the above automated system have problems in that it is expensive due to its complex structure, and has no protein purification function, like the RTS system, and it is difficult to produce several kinds of proteins.

Meanwhile, a sample containing a recombinant protein expressed by a cell culture or cell-free protein expression method contains various kinds of proteins in addition to a target protein. To easily purify the target protein from this sample, a technology of attaching an affinity tag (histidine tag) is used. In this technology, when a histidine tag encoding sequence is introduced into a template gene, the histidine tag is attached to the C or N terminus of a protein produced from the template gene, and the target protein can be easily obtained in high purity by isolating/purifying the protein using the affinity between the histidine tag and metal ions (nickel ions, cobalt ions, etc.).

However, the affinity tag that is used for purification can adversely affect the activity and structure of the target protein. For this reason, for the production of target proteins for protein function research and medical purposes, a process of removing the tag is required.

The present inventors (Bioneer) developed the automated protein synthesis system ExiProgen™ (Korean Patent Laid-Open Publication Nos. 10-2011-0121588 and 10-2013-0023091) and a related kit. This system is configured to automatically perform a cell-free protein expression reaction and purify an expressed protein. In this system, a template DNA and solutions required for a reaction can be automatically mixed in order to automatically perform a protein expression reaction, and can be maintained at a suitable temperature for the reaction. Also, all processes, including the synthesis of RNA from DNA and the expression of a protein from the RNA, can be maintained at the optimum temperature. Further, in order to easily purify a target protein from a mixture sample containing the expressed protein, an affinity tag such as oligohistidine is attached to the target protein, and in this state, the target protein is expressed, and is automatically purified using a magnetic bead having divalent metal ions (nickel ions, cobalt ions, etc.) attached thereto. The above ExiProgen™ and kit can simultaneously express and purify various kinds of proteins, but have problems in that, because protein expression is performed in a batch fashion, an energy source is exhausted with the passage of time, and is terminated by the accumulation of a protein expression inhibitor, and thus the level of a finally expressed protein is low.

In order to increase the expression level of a protein, a small-molecule expression solution containing triphosphate ribonucleic acid, an amino acid and an energy source should be continuously supplied, and protein expression inhibitors should be removed. In order to automatically perform such operations, new types of reactor and system are required.

The present inventors have made efforts to develop a system and a kit, which can overcome the shortcoming of low protein expression efficiency of the automated protein synthesizer ExiProgen™, and at the same time, increase the expression level of a target protein while eliminating the need to increase the size of the system due to the use of a small-molecule expression solution in an amount 10 times or more the amount of an expression solution. As a result, the present inventors have developed a system capable of increasing the expression level of a target protein by continuously supplying a small-molecule expression solution through a dialysis membrane during a cell-free protein expression reaction and removing protein expression inhibitors.

It was found that the system developed by the present inventors has the effect of increasing the efficiency of protein expression by automatically supplying a small amount of a small-molecule expression solution in several steps, can automatically purify an expressed protein, like the conventional system ExiProgen™, and can automatically replace a target protein solution, which contains a high-concentration eluate, with a desired protein storage buffer after purification.

In addition, the present inventors have found that, when a protein from which an affinity tag used for purification is to be removed is produced, a pure target protein can be produced by automatically removing the affinity tag by treatment with a protease, which recognizes and cleaves a specific amino acid sequence of the protein, during purification of the protein, thereby completing the present invention.

PRIOR ART LITERATURE

Patent Documents

Patent Document 1: Korean Patent Registration No. 10-0385298 B1 (May 13, 2003)
Patent Document 2: Korean Patent Registration No. 10-0534558 B1 (Dec. 1, 2005)
Patent Document 3: Korean Patent Registration No. 10-0733712 B1 (Jun. 23, 2007)
Patent Document 4: U.S. Patent Serial No. 2006-0257997 A1 (Nov. 16, 2006)

Non-Patent Documents

Cheolju Lee, et al., Development of High-Throughput Protein Production Technology, Ministry of Science and Technology, 17-30, 2005
Alexander Spirin & James R. Swartz, Cell-Free Protein Synthesis, p 103, FIG. 6.3B

DISCLOSURE OF INVENTION

Technical Problem

It is an object of the present invention to provide an automated cell-free protein production system that can increase the expression level of a target protein by automatically and continuously supplying a small amount of a small-molecule expression solution through a dialysis membrane in several steps during a cell-free protein expression reaction and removing protein expression inhibitors during the reaction, and a cell-free method for producing a protein using the system.

Technical Solution

To accomplish the above object the present invention provides an automated cell-free protein production system comprising: a protein expression reaction unit comprising a reaction vessel that includes a plurality of dialysis tubes, each including a dialysis membrane and being open at its top; a reaction temperature control unit configured to heat or cool the reaction vessel; a pipette array comprising a plurality of pipettes and configured to suck or discharge solutions using the pipettes; a pipette array moving unit configured to move the pipette array in an upward and downward direction, a forward and backward direction or a left and right direction so as to move solutions; a protein purification unit including a magnetic field application device; and a multi-well plate mounting unit having mounted therein a multi-well plate kit configured to supply solutions that are used for protein production.

The present invention also provides an automated cell-free protein production method comprising the steps of: (a)

preparing a cell-free protein expression mixture (S1); (b) expressing a protein using a small-molecule expression solution (S2); (c) purifying the protein using magnetic beads (S3); and (d) dialyzing the purified protein using a protein storage buffer (S4).

The present invention also provides an automated cell-free protein production method comprising the steps of: (a) preparing a cell-free protein expression mixture (S1); (b) expressing a protein using a small-molecule expression solution (S2); step (c') of purifying an affinity tag-free pure target protein (S3'); and (d) dialyzing the purified protein using a protein storage buffer (S4).

The present invention also provides a reaction kit for automated cell-free protein production, which comprises a multi-well plate kit comprising individual separate unit wells for storing a solution required for cell-free protein production, and a dialysis tube including a dialysis membrane.

BRIEF DESCRIPTION OF THE DRAWINGS

FIG. 8 is a flow chart (A) of an automated cell-free protein production method according to the present invention and a perspective view (B) of a multi-well plate kit according to the present invention.

(A): M: Bioneer AccuLadder™ Protein Size Marker (Low); E: expressed AcGFP sample; P: purified AcGFP sample; (B): M: Bioneer AccuLadder™ Protein Size Marker (Low); AcGFP: purified AcGFP sample; RFP: purified RFP sample; CAT: purified CAT sample; AcGFP (PCR Product): purified AcGFP-PCR product sample.

Figure 11:
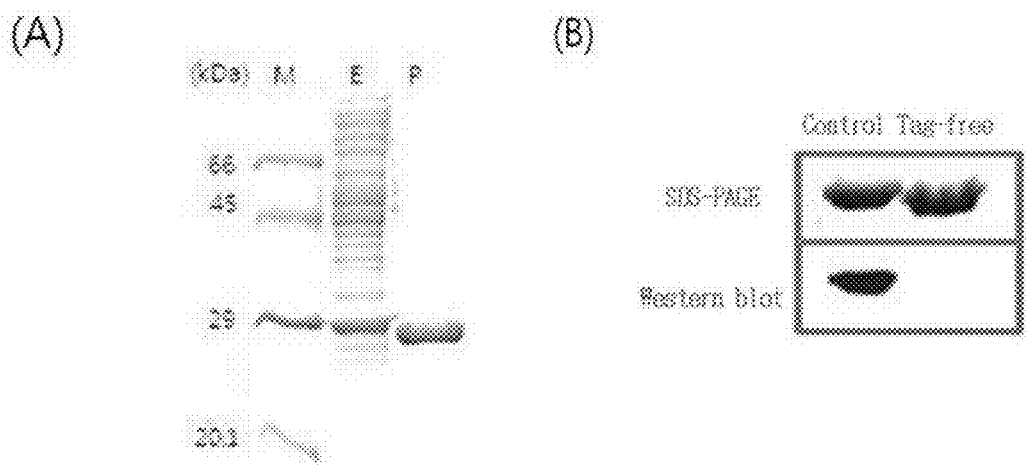

FIG. 11 shows the results of SDS-PAGE analysis and Western blotting of an affinity tag-free pure target protein produced according to the present invention.

(A): Results of SDS-PAGE of TEV-AcGFP; M: Bioneer AccuLadder™ Protein Size Marker (Low); E: expressed AcGFP sample; P: purified AcGFP sample; (B) comparison of samples according to the presence or absence of histidine tag; Control: TEV-AcGFP purified by an affinity-tagged target protein purification method; Tag-free: TEV-AcGFP sample purified by an affinity tag-free target protein purification method.

| Explanation on Symbols | |
|---|---|
| 10: automated cell-free protein production system | |
| 100: protein expression reaction unit | |
| 110: dialysis tube | 111: top structure |
| 112: dialysis membrane | 113: bottom structure |
| 114: elastic tube | 120: first reaction vessel |
| 121a: dialysis tube hole | |
| 121b: small-molecule expression solution hole | |
| 122a: dialysis tube hole | 122b: dialysis solution hole |
| 130: first reaction vessel cover | 131: hole |
| 132: evaporation preventing film | |
| 140: second reaction vessel | |
| 141a: dialysis tube hole | |
| 141b: small-molecule expression solution hole | |
| 150: second reaction vessel cover | 151: hole |
| 152: evaporation preventing film | |
| 160: third reaction vessel | |
| 161: small-molecule expression solution vessel | |
| 162: solution vessel cover | |
| 163: inlet | 164: outlet |
| 165: metering pump | 166: multi-channel valve |
| 167: solution container | 168: control valve |
| 169: waste container | 170: fourth reaction vessel |
| 171: small-molecule expression solution vessel | |
| 172: solution vessel cover | |
| 173: solution passage | 174: bidirectional metering pump |
| 175: multi-channel valve | 176: solution container |
| 177: waste container | |
| 180: reaction temperature control unit | |
| 190: magnetic field application device | 191: magnet |
| 192: magnet mounting unit | 200, 200': multi-well plate kit |
| 300: pipette array | 310: pipette |
| 320: pipette array moving unit | |
| 400: protein purification unit | |
| S1 to S4: automated cell-free protein production method | |

EMBODIMENTS OF THE INVENTION

Unless defined otherwise, all technical and scientific terms used herein have the same meaning as commonly understood by one of ordinary skill in the art to which the invention pertains. Generally, the nomenclature used herein and the experiment methods are those well known and commonly employed in the art.

In one aspect, the present invention is directed to an automated cell-free protein production system comprising: a protein expression reaction unit comprising a reaction vessel that includes a plurality of dialysis tubes, each including a dialysis membrane and being open at its top; a reaction temperature control unit configured to heat or cool the reaction vessel; a pipette array comprising a plurality of pipettes and configured to suck or discharge solutions using the pipettes; a pipette array moving unit configured to move the pipette array in an upward and downward direction, a forward and backward direction or a left and right direction so as to move solutions; a protein purification unit including a magnetic field application device; and a multi-well plate mounting unit having mounted therein a multi-well plate kit configured to supply solutions that are used for protein production.

Each of the dialysis tubes comprises: a cylindrical dialysis membrane having a predetermined length; a bottom structure fitted in the bottom of the dialysis membrane and having a disk shape; and a top structure fitted in the top of the dialysis membrane and being a ring structure having a T shape.

Each of the dialysis tubes further comprises elastic tubes fitted around the outer peripheral surface of portions of the dialysis membrane, which come in contact with the top structure and the bottom structure.

The reaction vessel further comprises a reaction vessel cover configured to cover the reaction vessel to prevent evaporation of solution from the dialysis tubes, the reaction vessel cover having a plurality of incisions that allow the pipettes to be inserted into the dialysis tubes.

The protein expression reaction unit comprises: a plurality of dialysis tube holes formed in the top thereof and configured to receive the dialysis tubes; and a plurality of small-molecule expression solution holes formed adjacent to the dialysis tube holes so as to fluidically communicate with the dialysis tube holes.

The protein expression reaction unit further comprises a protein dialysis unit including: a plurality of dialysis tube holes formed in the top thereof and configured to receive the dialysis tubes; and a plurality of dialysis solution holes formed adjacent to the dialysis tube holes so as to fluidically communicate with the dialysis tube holes and configured to receive a protein storage buffer.

The protein expression reaction unit comprises: an openable/closable outlet configured to allow a solution to be discharged from the reaction vessel therethrough; a waste container connected to the outlet so as to fluidically communicate with the outlet; an inlet configured to allow a solution to be introduced into the reaction vessel therethrough; a metering pump configured to supply a solution into the inlet; and one or more solution containers connected to the metering pump.

The protein expression reaction unit further comprises a multi-channel valve configured such that one side thereof is connected with the metering pump and the other side thereof fluidically communicates with any one selected from among the solution containers.

The protein expression reaction unit comprises: a solution passage configured to allow a solution to be supplied or discharged to or from the reaction vessel therethrough; a bidirectional metering pump connected with the solution passage and configured to supply or discharge a solution to or from the reaction vessel; one or more solution containers connected with the bidirectional metering pump; one or more waste containers connected with the bidirectional metering pump; and a multi-channel valve configured such that one side thereof is connected with the bidirectional metering pump and the other side thereof is connected with the solution containers and the waste containers, so that any one selected from among the solution containers or the waste containers fluidically communicate with the bidirectional metering pump through the multi-channel valve.

The pipette array comprises 1 to 96 pipettes arranged in 1 to 12 rows according to the size of the reaction vessel and the number of the pipettes, and is configured to allow the pipettes to be automatically attached or detached thereto or therefrom and is configured to suck and discharge a desired amount of a solution.

Hereinafter, the present invention will be described in further detail.

Figure 1:
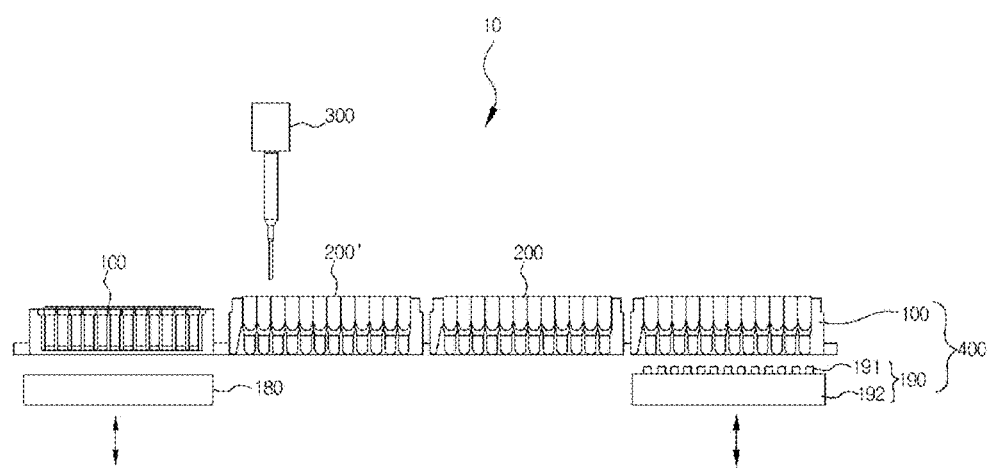
FIG. 1 is a schematic view of an automated cell-free protein production system according to the present invention.

FIG. 1 illustrates the overall configuration of an automated cell-free protein production system 10 according to the present invention.

Referring to FIG. 1, the automated cell-free protein production system of the present invention comprises a protein expression reaction unit 100, a reaction temperature control unit 180, a pipette array 300, a pipette array moving unit 320, a protein purification unit 400, and a multi-well plate mounting unit capable of being mounted with multi-well plate kits 200 and 200'.

The protein expression reaction unit 100 is a vessel having a plurality of grooves in which dialysis tubes 110 comprising a cylindrical dialysis membrane 112 and open at the top can be disposed such that the upper portion thereof is exposed to the outside of the grooves and they are arranged at a predetermined distance from one another in vertical and horizontal directions. The vessel can receive a small-molecule expression solution or the like. The protein expression reaction unit 100 comprises a reaction vessel 120, 140, 160 or 170 configured to automatically add and remove the small-molecule expression solution so as to come into contact with the outside of the dialysis membrane 112.

The reaction temperature control unit 180 is placed under the reaction vessel 120, 140, 160 or 170 and serves to heat or cool the reaction vessel 120, 140, 160 or 170.

The pipette array 300 comprises a plurality of pipettes 310 having the same arrangement as that of a plurality of dialysis tubes 110 that are inserted in the protein expression reaction unit 100, and it is configured to suck or discharge a solution using the pipettes 310.

The pipette array moving unit 320 is configured to move the pipette array 300 in an upward and downward direction, a forward and backward direction or a left and right direction so as to move a solution from the protein expression reaction unit, the multi-well plate kit or the like.

The protein purification unit 400 comprises a magnetic field application device 190 configured to attach an expressed target protein to a magnetic bead and then attach the magnetic bead to a wall.

The magnetic field application device 190 comprises a magnet mounting unit 192 having a magnet 191 mounted thereon, and serves to move the magnet mounting unit 192 upward or downward to apply or remove a magnetic field.

In addition, the reaction temperature control unit 180 and the magnetic field application device 190 may be constructed separately, or may be constructed so as to be simultaneously controlled at the same position. In other words, as shown in the drawings, the protein purification unit 400 is not provided separately, but each of the reaction vessels 120, 140, 160 and 170 may include both the protein expression reaction unit 100 and the protein purification unit 400, and the reaction temperature control unit 180 and the magnetic field application device 190 may be moved and located under each reaction vessel.

Hereinafter, the configuration of the dialysis tube 110 of the present invention will be described in detail with reference to FIG. 2.

Figure 2:
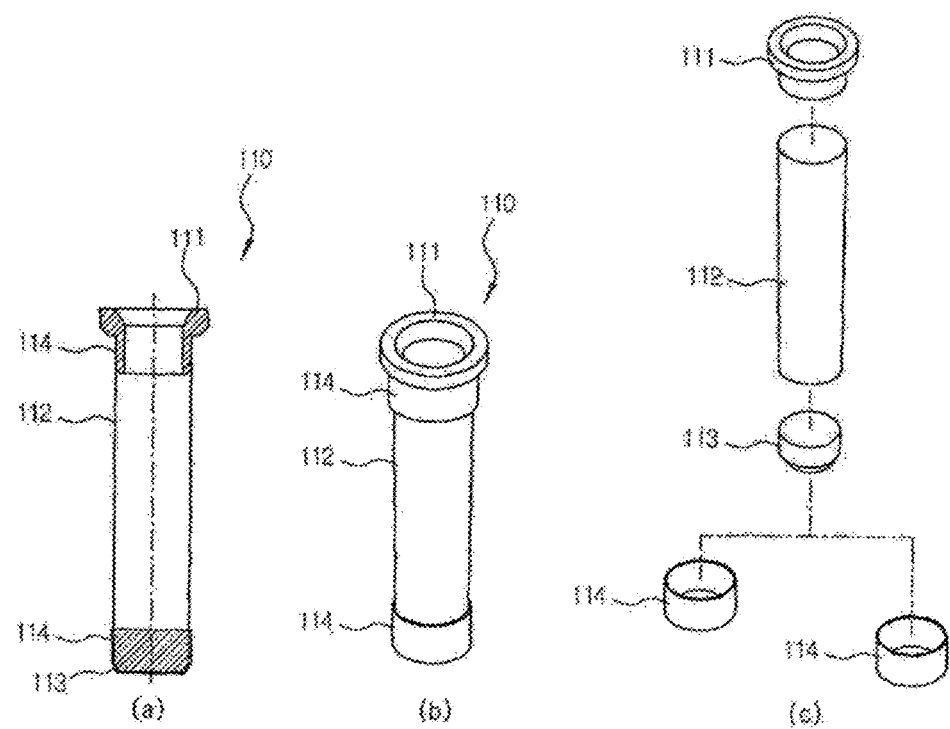
FIG. 2 shows a cross-sectional view (a), perspective view (b) and exploded view (c) of a dialysis tube according to the present invention.

Referring to FIG. 2, the dialysis tube 110 of the present invention comprises a dialysis membrane 112, a bottom structure 113, a top structure 111, and an elastic tube 114.

The dialysis membrane 112 is formed in a cylindrical shape having a predetermined length, and the bottom structure 113 has a disk shape and is inserted in the bottom of the dialysis membrane. Also, the top structure 111 is a ring structure having a T-shape, is inserted in the top of the dialysis membrane 112, and has a hole into which a solution can be introduced.

The dialysis tube 110 preferably includes an elastic tube 114 disposed around the outsides of portions of the dialysis membrane 112, which come in contact with the top structure 111 and the bottom structure 113 in order to increase the adhesion therebetween.

Also, the top structure 111 has a diameter larger than that of the bottom of the dialysis tube 110 so that it can be stopped by the upper end of the dialysis tube hole 121a or 141a of the reaction vessel 120, 140, 160 or 170 when the dialysis tube 110 is inserted into dialysis tube hole.

More specifically, in order to mount the dialysis tube 110 in accordance with the 96-well standard format, the top structure 111 preferably has a diameter of 9 mm or less, and the dialysis membrane 112 preferably has a diameter of 6.37 mm or 7.62 mm.

In the prior art, a dialysis membrane is provided at the bottom of a reaction vessel, whereas, in the present invention, the dialysis membrane 112 is cylindrical in shape, and thus has an increased area of contact with a small-molecule expression solution, thus enabling a reaction to be performed efficiently.

Hereinafter, the configuration of the reaction vessels 120, 140, 160 and 170 of the present invention will be described in detail with reference to FIGS. 3 to 6.

Figure 3:
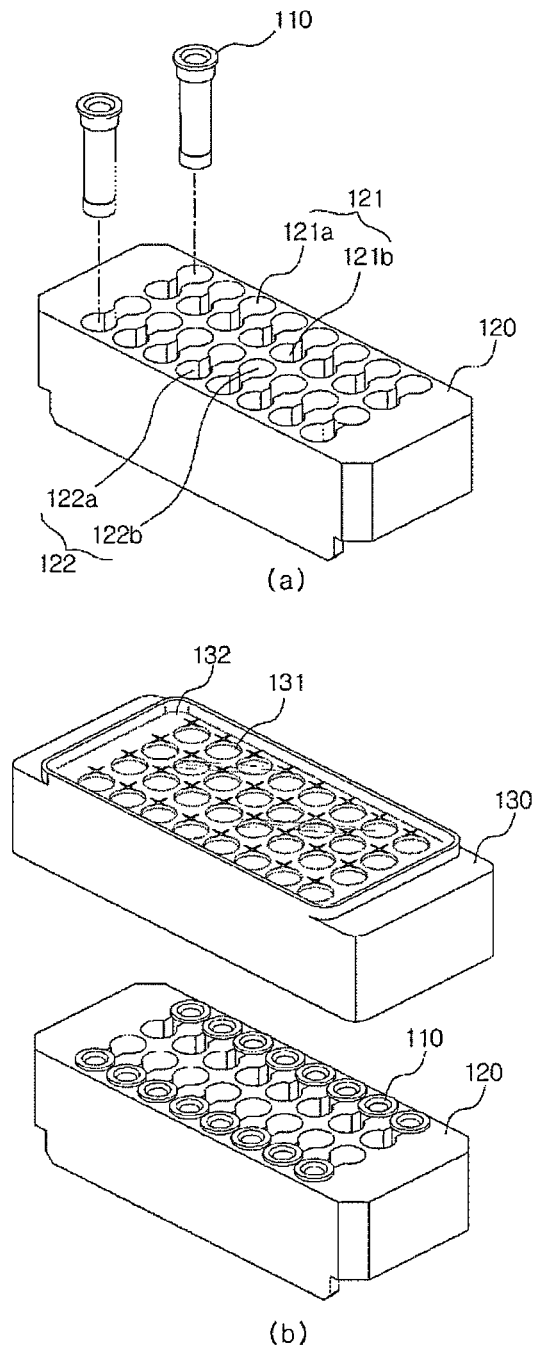
FIG. 3 shows a perspective view and exploded view of a first reaction vessel according to the present invention.
Figure 4:
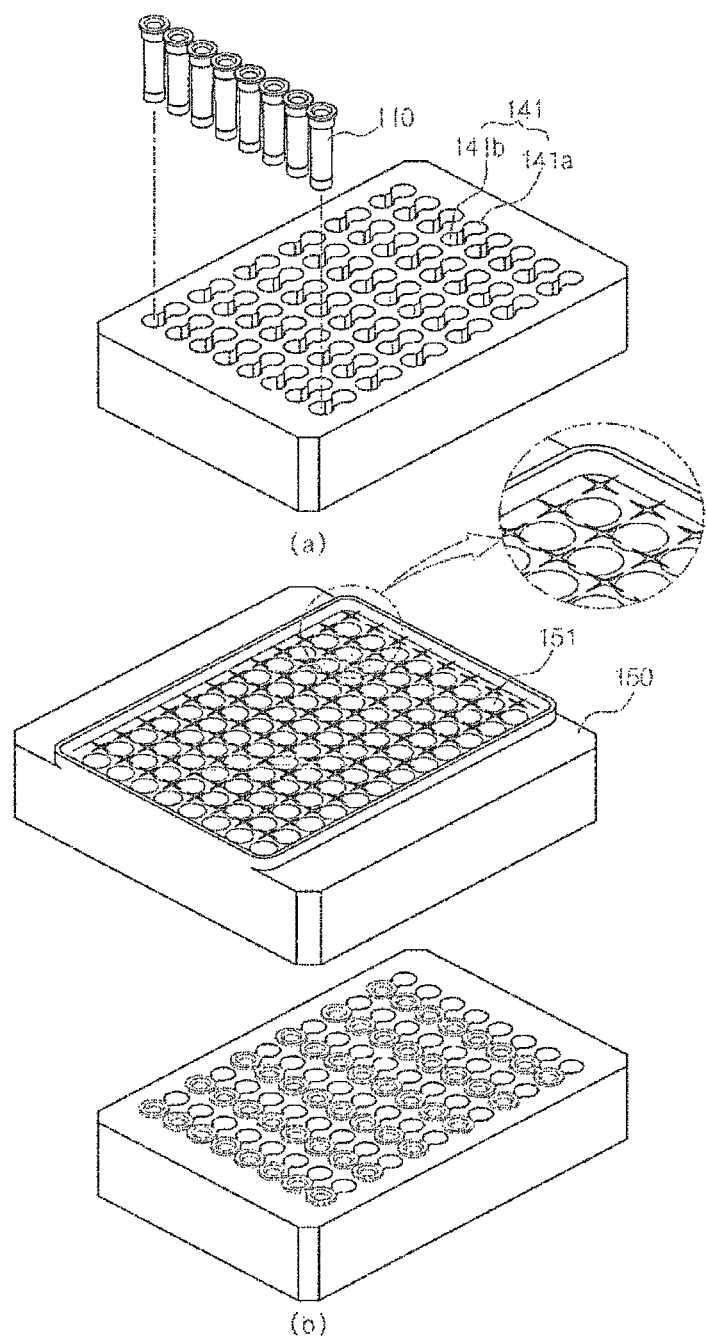
FIG. 4 shows a perspective view and exploded view of a second reaction vessel according to the present invention.
Figure 5:
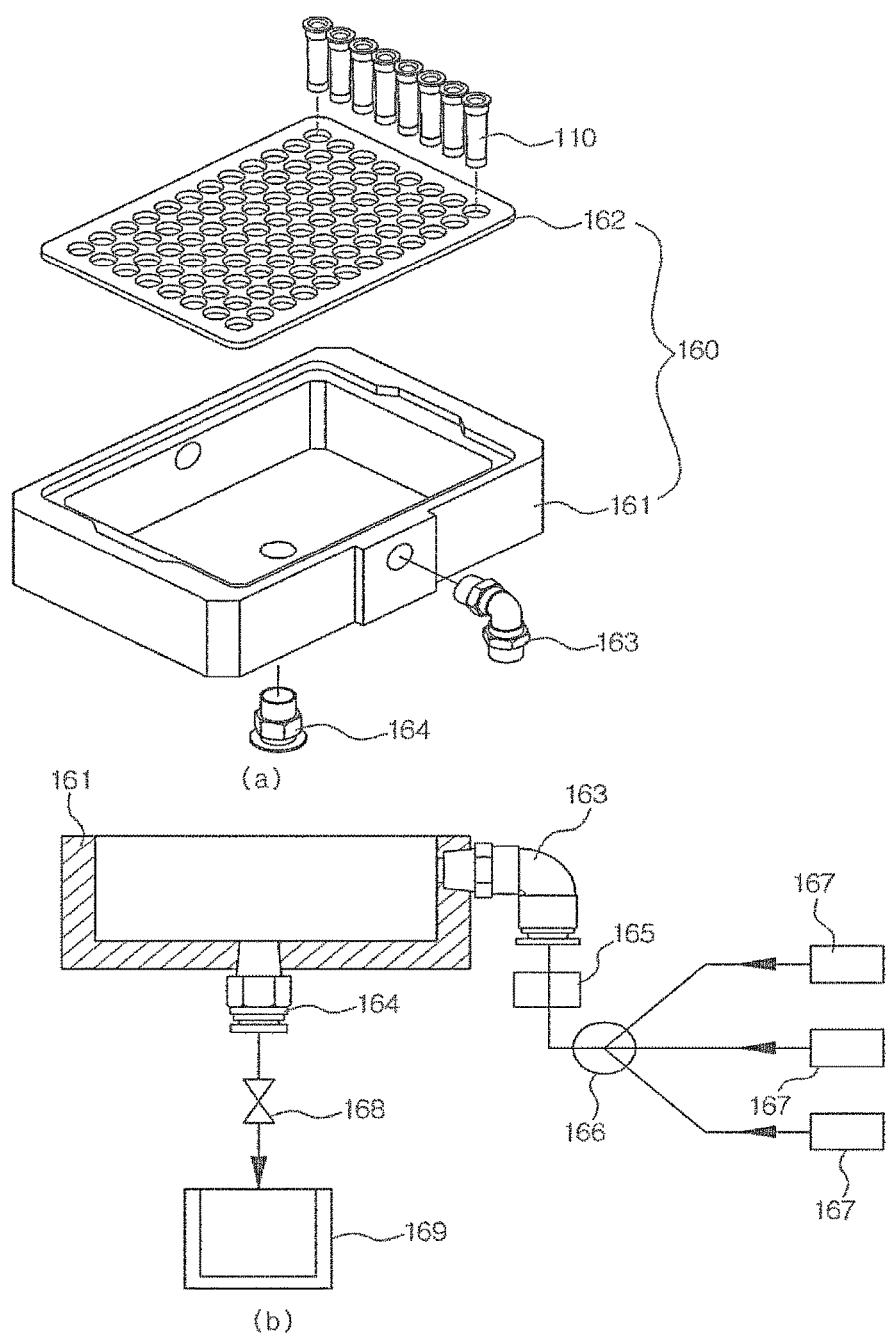
FIG. 5 shows a perspective view and exploded view of a third reaction vessel according to the present invention.
Figure 6:
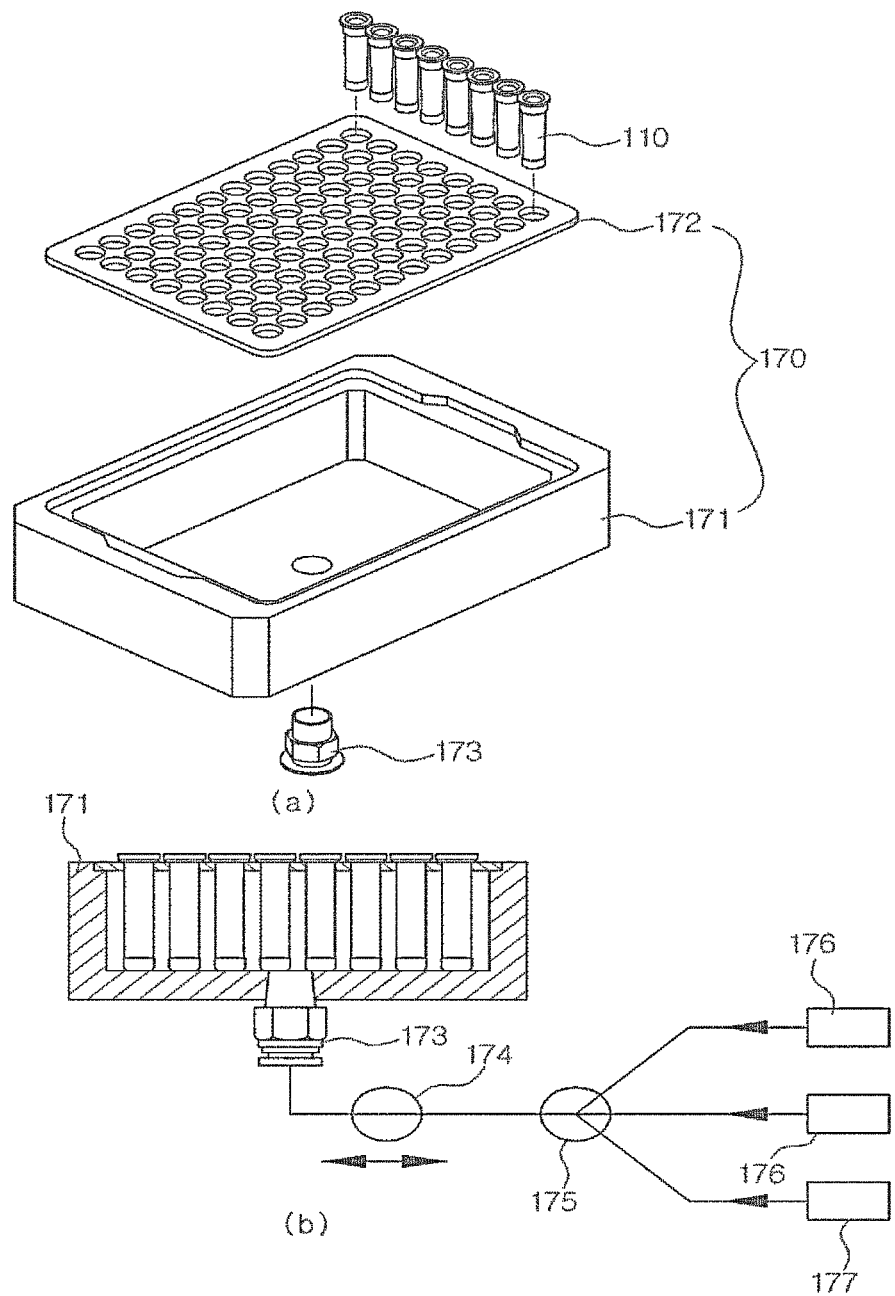
FIG. 6 shows a perspective view and exploded view of a fourth reaction vessel according to the present invention.

FIGS. 3 to 6 show various embodiments of the reaction vessels 120, 140, 160 and 170 of the present invention. Specifically, FIG. 3 shows a first reaction vessel 120 capable of receiving 16 dialysis tubes; FIG. 4 shows a second reaction vessel 140 capable of receiving 48 dialysis tubes; FIG. 5 shows a third reaction vessel 160 capable of receiving 96 dialysis tubes; and FIG. 6 shows a fourth reaction vessel 170 capable of receiving 96 dialysis tubes.

The first reaction vessel 120 and the second reaction vessel 140 are configured such that a small-molecule expression solution hole 121b or 141b capable of receiving a small-molecule expression solution is formed to fluidically communicate with the dialysis tube. The third reaction vessel 160 and the fourth reaction vessel 170 are configured such that a space capable of receiving the small-molecule expression solution is formed therein and the small-molecule expression solution, a protein storage buffer or the like can be supplied thereto or recovered therefrom using a pump 165 or 174.

Referring to FIG. 3, the first reaction vessel 120 will now be described in detail.

In the first reaction vessel 120, there are formed a plurality of dialysis tube holes 121a into which the dialysis tube 110 is inserted, and there are formed a plurality of small-molecule expression solution holes 121b that are adjacent to the dialysis tube holes 121a and fluidically communicate with the dialysis tube holes 121a. Preferably, the number of the dialysis tube holes 121a is 16 so that 16 dialysis tubes 110 can be received therein.

Also, the first reaction vessel 120 is configured such that is divided into a protein expression reaction unit 100 that receives 8 dialysis tubes 110 and performs protein expression, and a protein dialysis unit 122 that dialyzes a purified protein using a protein storage buffer.

The protein dialysis unit 122 comprises: a plurality of dialysis tube holes 122a into which the dialysis tube 110 is inserted; and a plurality of dialysis solution holes 122b that are formed adjacent to the dialysis tube holes 122a so as to fluidically communicate with the dialysis tube holes 122a, and are capable of receiving a protein storage buffer.

Also, the first reaction vessel 120 further comprises a first reaction vessel cover 130 in order to prevent a solution in the dialysis tube 110 from evaporating.

The first reaction vessel cover 130 has holes 131 formed to correspond to the small-molecule expression solution holes 121b and dialysis tube holes 121a formed in the reaction vessel 120. Also, above the holes 131, there is provided a evaporation preventing film 132 in order to prevent a solution in the dialysis tube 110 from evaporating. In addition, portions of the evaporation preventing film 132, which correspond to the small-molecule expression solution holes 121a and the dialysis tube holes 121b, may be incised so that pipettes 310 can be easily inserted therethrough. These portions are preferably incised in a "±" shape, but are not limited thereto.

Referring to FIG. 4, the second reaction vessel 140 of the present invention will be described in detail.

The second reaction vessel 140 has dialysis tube holes 141a in which the dialysis tube is inserted, and small-molecule expression solution holes 141b that are formed adjacent to the dialysis tube holes 141a so as to fluidically communicate with the dialysis tube holes 141a. Preferably, the number of the dialysis tube holes 141a is 48 so that 48 dialysis tubes 110 can be received therein. Herein, some of the small-molecule expression solution holes may be used as a protein dialysis unit.

Also, the second reaction vessel 140 further comprises a second reaction vessel cover 150 in order to prevent a solution in the dialysis tube 110 from evaporating.

The second reaction vessel cover 150 has holes 151 formed to correspond to the small-molecule expression solution holes 141b and dialysis tube holes 141a formed in the second reaction vessel 140. Above the holes 151, there is formed an evaporation preventing film 152 in order to prevent a solution in the dialysis tube 10 from evaporating. Also, portions of the evaporation preventing film 152, which correspond to the small-molecule expression solution holes 141b and the dialysis tube holes 141a, may be incised so that the pipettes 310 can be easily inserted therethrough. Preferably, these portions are incised in a "±" shape, but are not limited thereto.

Referring to FIG. 5, the third reaction vessel 160 of the present invention will be described in detail.

The third reaction vessel 160 comprises: a small-molecule expression solution vessel 161 having a space capable of receiving a small-molecule expression solution or a protein storage buffer; and a solution vessel cover 162 that serves as cover the small-molecule expression solution vessel 161 and has dialysis tube holes in which the dialysis tube 110 is inserted. Preferably, the number of the dialysis tube holes is 96 so that 96 dialysis tubes 110 can be received therein.

Further, the third reaction vessel 160 comprises an inlet 163 configured to introduce a small-molecule expression solution or a protein storage buffer, and an outlet 164 configured to discharge a small-molecule expression solution or a protein storage buffer after completion of a reaction.

The inlet 163 is connected to a metering pump 165, a multi-channel valve 166 and at least one solution container 167. Specifically, in order to introduce a small-molecule expression solution or a protein storage buffer into the inlet 163, the multi-channel 166 is connected to at least one of the solution containers 167, and a small-molecule expression solution or a protein storage buffer in the solution container 167 is supplied into the third reaction container 160 by means of the metering pump 165.

The outlet 164 is connected to a control valve 168 and a waste container 169. When a small-molecule expression solution or a protein storage buffer is to be introduced into the third reaction vessel 160, the control valve 168 is closed, and the reaction of the small-molecule expression solution or protein storage buffer in the reaction vessel 160 occurs, and after a certain time, the reacted small-molecule expression solution or protein storage buffer is recovered into the waste container 169 by opening the control valve 168.

The position at which the outlet 164 is disposed is not limited, but the outlet 164 is preferably disposed under the reaction vessel 160 so that the small-molecule expression solution will be discharged into the outlet 164 by gravity without needing a separate pump. Also, the bottom surface of the reaction vessel 160 is preferably inclined toward the outlet 164 so that the small-molecule expression solution will easily flow out. In addition, when the outlet is disposed at the side of the reaction vessel, a pump may also be disposed in order to discharge the solution.

Referring to FIG. 6, the fourth reaction vessel 170 will be described in detail.

The fourth reaction vessel 170 is configured in the same manner as the third reaction vessel 160. However, a solution is discharged or introduced through the outlet 164 and the inlet 163, but a solution passage 173 is disposed in the fourth reaction vessel 170 so that a solution will be introduced or discharged through a single hole.

FIG. 6 shows that the solution passage is disposed at the bottom, but is not limited, and the solution passage may be disposed at any position for the introduction or discharge of a solution.

The solution passage 173 is connected with a bidirectional metering pump 174, a multi-channel valve 175, a waste container 177 and a solution container 176. The multi-channel valve 175 functions the waste container 177 to at least one of the solution containers 176. Also, the bidirectional metering pump 174 is a pump capable of introducing a solution in both directions.

More specifically, when a small-molecule expression solution or a protein storage solution is to be introduced into the fourth reaction vessel 170, the multi-channel valve 175 is opened, and one selected from among the solution containers 176 is opened, and the bidirectional metering pump 174 introduces the small-molecule expression solution or the protein storage solution from the solution container 176 into the fourth reaction container 170. Conversely, when the small-molecule expression solution or the protein storage solution is to be discharged from the fourth reaction container 170, the multi-channel valve 175 opens the waste container 177, and the bidirectional metering pump 174 discharges the reacted small-molecule expression solution or protein storage solution from the fourth reaction vessel 170 into the waste container 177.

Even in the case where the reaction container 120, 140, 160 or 170 has any configuration (any of the embodiments shown in FIGS. 3 to 6), an additional dialysis process for stabilization of a purified protein can be automatically performed. Using a magnetic bead that binds to an affinity tag, a protein is attached and washed to remove substances other than the target protein. Then, in order to elute the attached target protein from the magnetic bead, an elution buffer containing a high concentration of an eluent should be added. A process of removing this elution buffer as soon as possible and replacing the purified protein with a stable buffer is required, and this process can be automatically performed either the pipette array 300 or the pump 165, 174 and the multi-channel valve 166, 175.

Hereinafter, the effects of the reaction vessel 120, 140, 160 or 170 of the present invention will be described in detail.

The present inventors have attempted to design the well-type reaction vessel 120, 140, 160 or 170 and a desired number of dialysis tubes including dialysis membranes, which can be mounted therein. Also, the present inventors have attempted to complete a protein expression reaction unit capable of expressing the highest possible level of a target protein using a minimum amount of a small-molecule expression solution, and to perform a method that maximizes the level of protein expression by a minimum amount of a small-molecule expression solution using a method of adding a cell-free small-molecule protein expression solution in several steps.

It was reported that, when the concentration of reaction products (expression reaction inhibitors) produced during the progression of a protein expression reaction is reduced through a dialysis membrane, the reaction is continuously carried out. Herein, it was reported that a small-molecule expression solution corresponding to at least 10 times the volume of the reaction solution should be used to maximize the reaction. In other words, for a protein expression reaction having a volume of 0.5 ml, a small-molecule expression solution having a volume of 5 ml or more and a reaction vessel capable of reacting it are required. When this volume is used, there is a problem in that the size of a reaction vessel for expressing a plurality of proteins increases, leading to an increase in the size of an automated system.

In the present invention, it was attempted to overcome this problem by adding a small amount of a small-molecule expression solution and replacing it in multiple steps.

Theoretically, given c is the concentration of expression reaction inhibitors produced during a reaction, v (ml) is the volume of the reaction solution, and V (ml) is the volume of a small-molecule expression solution, the concentration of expression reaction inhibitors remaining in a reaction solution when a complete equilibrium is reached through a dialysis membrane is $$c\frac{v}{v+V}.$$

If a 9-fold volume of the small-molecule expression solution is used (V=9 v), the concentration will be 0.1c, and thus the reaction will be performed by 10c until the concentration will reach c. For example, if dialysis is performed stepwise at V=v, the concentration will be 0.5c in step 1, and thus the reaction will be performed by 2c until the concentration will reach c. When the small-molecule expression solution that reached the c concentration is removed and a fresh small-molecule expression is added, the concentration will also be 0.5c in step 2, and thus the reaction will be performed by 2c until the concentration will reach c. If this process is repeatedly performed in 8 steps, the reaction will be performed by 10c, and thus a protein corresponding to 10 times can be obtained. Thus, when this method is used, the size of the reaction vessel is reduced to ⅕, and thus the overall size of the system can be reduced.

This method of replacing a solution in multiple steps is more effective in a dialysis step that is the final step of a process production process. Given the concentration of a first eluate is c, the volume of a reaction solution is v ml and the volume of buffer is V ml, the concentration of the final eluate remaining in the reaction solution is $$c\frac{v}{v+V}.$$

If a 9-fold volume of buffer is used (V=9 v), the concentration may reach 0.1c. For example, if dialysis is performed stepwise at V=v, it will be achieved in step 1 to reach equilibrium, and thus the concentration will become 0.5c.

When the buffer that reached a concentration of 0.5c is removed and a fresh buffer is added, the concentration will reach 0.25c in step 2, and reach 0.125c in step 3. Thus, dialysis can be performed even with ⅓ of buffer at a similar concentration.

The present inventors have competed a protein expression reaction unit 10 capable of expressing a target protein at the highest possible level by an expression reaction with a minimum amount of a small-molecule expression solution, by designing a reaction vessel 120, 140, 160 or 170 allowing the small-molecule expression solution to be replaced stepwise. Thus, the present invention provides an automated cell-free protein production system, which can purify a synthesize protein, is more compact, and can produce a larger amount of a protein in a more efficient manner, compared to the prior art.

Figure 7:
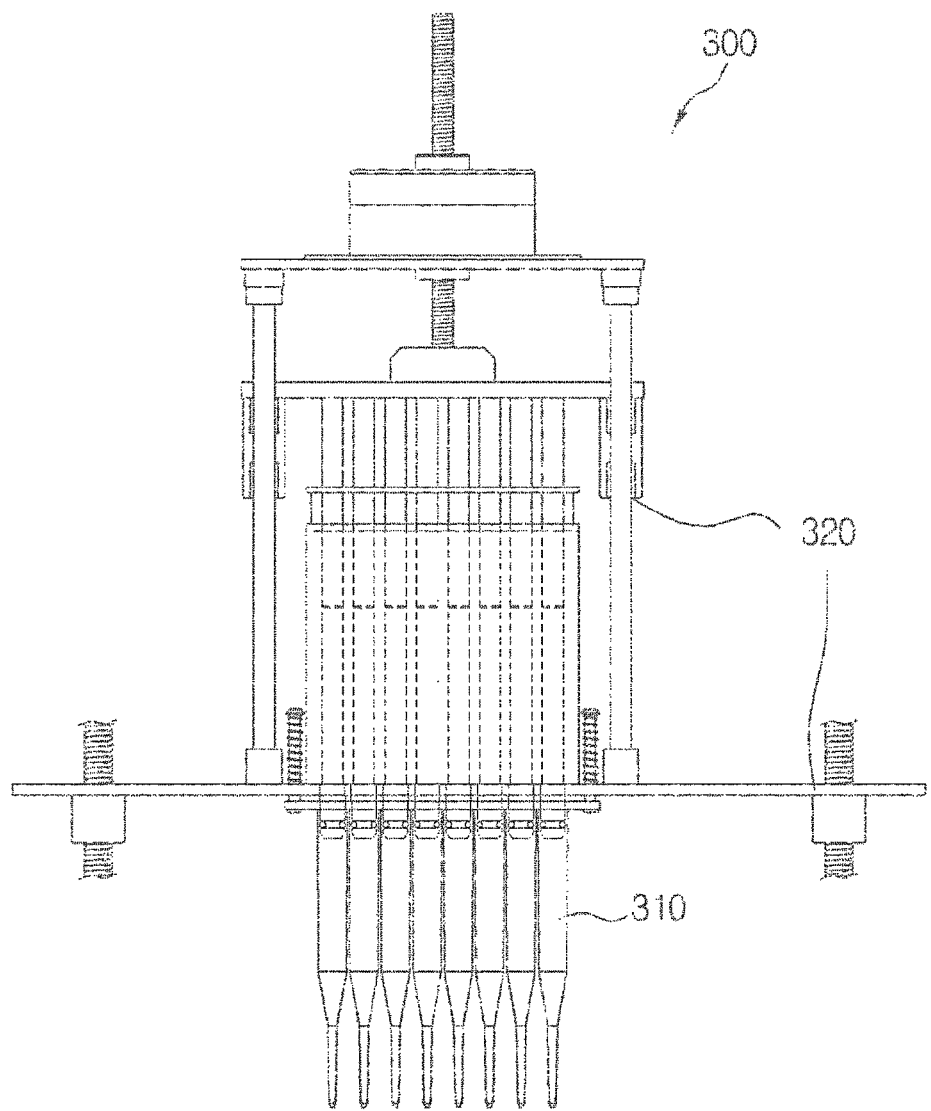
FIG. 7 is a front view of a pipette array according to the present invention.

Referring to FIG. 7, the pipette array 300 of the present invention will be described.

The pipette array 300 is an automated pipette array 300 that allows 1 to 96 pipettes 310 to be attached or detached, and can quantitatively suck and discharge a desired volume of a solution. In the pipette array 300, pipettes are arranged in 1 to 12 rows, each consisting of 8 pipettes. FIG. 8 shows a pipette array in which 8 pipettes can be mounted. The pipette array 300 is moved by a pipette array moving unit 302 in an upward and downward direction, a forward and backward direction or a left and right direction, and the pipette array 300 and the pipette array moving unit 320 are described in detail in Korean Patent No. 10-1025135 and Korean Patent Laid-Open Publication No. 10-2011-0121588.

Referring to FIG. 8, an automated cell-free protein production method and a multi-well plate kit 200 or 200' according to the present invention will be described.

The automated cell-free protein production method of the present invention comprises the steps of: (a) preparing a cell-free protein expression mixture (S1); (b) expressing a protein using a small-molecule expression solution (S2); (c) purifying the protein using magnetic beads (S3); and (d) dialyzing the purified protein using a protein storage buffer (S4).

Also, step (c) of purifying the protein using a magnetic bead (S3) is a step of purifying an affinity-tagged target protein, and may be changed to step (c') of purifying an affinity tag-free pure target protein (S3').

The automated cell-free protein production method of the present invention is preferably performed by the automated cell-free protein production system as described above, but is not limited thereto.

In the present invention, step (b) of expressing the protein may comprise the steps of: (i) introducing a small-molecule expression solution; (ii) promoting the expression of a protein; and (iii) removing the small-molecule expression solution.

Herein, the small-molecule expression solution may be supplied from a multi-well plate kit or a solution container, and a large amount of a protein can be expressed by sequentially repeating steps (i) to (iii) once or more.

In the present invention, step (c) of purifying a protein using magnetic beads may comprise the steps of: (i) binding the expressed protein product to magnetic beads; (ii) introducing a magnetic bead washing solution and applying/removing a magnetic field to remove impurities from the magnetic bead; and (iii) isolating a target protein from the magnetic bead.

When step (c) of purifying the protein using a magnetic bead is changed to step (c') of purifying an affinity tag-free pure target protein (S3'), step (c') may comprise: (i) binding the expressed protein product to magnetic beads; (ii) removing impurities from the magnetic beads by supplying a magnetic bead washing solution and applying/removing a magnetic field; (iii) supplying a protease and a protease reaction buffer; (iv) removing an affinity tag, bound to the magnetic beads, from the target protein; and (v) binding the protease to the magnetic beads to isolate and recover the target protein.

Herein, the magnetic bead suspension, the magnetic bead washing solution, the protein elution buffer or the protease reaction buffer may be supplied from the multi-well plate kit, and step (ii) of removing impurities from the magnetic beads by supplying the magnetic bead washing solution may be repeated once or more.

In the present invention, step (d) of dialyzing the purified protein using the protein storage buffer may comprise: (i) supplying the protein storage buffer into a dialysis solution hole; and (ii) removing the protein elution buffer or protease reaction buffer from the dialysis tube.

Herein, the protein storage buffer may be supplied from the multi-well plate kit or the solution container, and step (i) of introducing the protein storage buffer into the dialysis solution hole, and step (ii) of removing the protein elution buffer or the protease reaction buffer from the dialysis tube may be sequentially repeated once or more.

In another aspect, the present invention is directed to a reaction kit for automated cell-free protein production. The reaction kit for automated cell-free protein production comprising: a multi-well plate kit comprising individual separate unit wells for storing a solution required for cell-free protein production.

Also, the multi-well plate kit may comprise a solution required for cell-free protein production. Herein, the required solution may be one or more selected from among protein storage buffer, sterile distilled water, a magnetic bead suspension, a magnetic bead washing solution, a protein elution buffer, a small-molecule expression solution, a protease reaction buffer, solutions containing liposomes or micelles for membrane protein synthesis, etc., but is not limited thereto. Any person skilled in the art may prepare a solution for cell-free protein synthesis and purification. The multi-well plate kit is configured such that the kind of solution and the unit wells being dispensed vary depending on the purpose of cell-free protein synthesis and purification.

Further, the reaction kit for automated cell-free protein production may further comprise a dialysis tube including a dialysis membrane.

In addition, the small-molecule expression solution or protein storage buffer may be supplied from the solution container 167 or 176, and in this case, it can be repeatedly added using a pump, and can be discharged through the waste container 169 or 177 after completion of a reaction.

Also, the magnetic beads that are used for protein purification may be magnetic beads having bound thereto divalent metal ions such as nickel ions or cobalt ions.

The present invention is also intended to provide a target protein by disposing the dialysis tubes 110 in the protein expression reaction unit 100 of the automated cell-free protein production system 10, introducing a protein expression mixture into the dialysis tubes, periodically adding a small-molecule expression solution to the outside of the dialysis tubes 10 to allow cell-free protein expression to occur continuously, purifying the automatically expressed protein in the automatic protein purification unit 400 provided with the magnetic field application device 190 using magnetic beads that bind with an affinity tag, and dialyzing the purified protein solution with a protein storage buffer in the protein dialysis unit 22.

Also, the multi-well plate kit 200, 200' that is used in the present invention comprises a first multi-well plate kit 200 and a second multi-well plate kit 200'.

The first multi-well plate 200 comprises: a plurality of unit well A, B, C, D, E and F, each consisting of two adjacent rows; and a film (not shown) sealing the top of the plurality of unit wells A, B, C, D, E and F. The second multi-well plate kit 200' comprises: a plurality of unit wells G, H, I, J, K and L, each consisting of two adjacent wells; and a film (not shown) sealing the top of the plurality of unit wells G, H, I, J, K and L.

Although each of the multi-well plate kits 200 and 200' comprises each unit well consisting of two rows as described above, it may be divided into spaces that store solutions, according to the number of reaction vessels and pipettes that can be disposed.

Also, the multi-well plate kit 200 or 200' includes a small-molecule expression solution required for protein expression, a magnetic bead suspension required for protein purification, a magnetic bead washing solution, a protein storage buffer, etc.

More specifically, solutions required for protein purification may include a magnetic bead suspension for attaching a target protein, a washing solution for removing those other than the target protein from the magnetic beads, an elution buffer for detaching the target protein from the magnetic beads, a protease reaction buffer required for removing an affinity tag from the target protein, a protein storage buffer, sterile distilled water, a small-molecule expression solution, a membrane protein synthesis solution, etc.

The solution that is introduced into the unit well of each of the multi-well plate kits 200 and 200' may vary according to the intended use.

As used herein, the term "template DNA" refers to a nucleic acid strand to be replicated when new DNA or RNA is produced by DNA or RNA polymerization using DNA polymerase or RNA polymerase. It may be a DNA in a circular form or a linear form. Preferably, the circular DNA may be a plasmid DNA, and the linear DNA may be a PCR product, but is not limited thereto.

In the method of the present invention, a template DNA may be easily obtained as a DNA sequence comprising a target protein gene sequence and an enzyme cleavage site sequence in a vector, which can express a protein, by a conventional gene recombination method, and this method is obvious to those skilled in the art.

In the method of the present invention, the protein expressed from the template can be expressed in the order of either target protein-enzyme cleavage site-enzyme cleavage site-affinity tag or affinity tag-enzyme cleavage site-target protein. The enzyme cleavage site is cleaved by protease so that the affinity tag can be separated from the target protein, and thus only the target protein can be finally obtained.

As used herein, the term "affinity tag" may be defined as a fusion partner comprising a substance having the ability to bind to a specific ligand. It is generally used for protein purification.

In the method of the present invention, the affinity tag may use (i) β-galactosidase, glutathione S transferase (GST) having selective affinity with the substrate, (ii) protein A protein having selective affinity for IgG, or (iii) polyhisitidine having an affinity for a metal such as $Cu^{2+}$, $Ni^{2+}$ or $Co^{2+}$. Preferably, the affinity tag may be histidine or cysteine, but is not limited thereto.

In the method of the present invention, magnetic beads may be used.

In the present invention, the affinity tag may be easily inserted by selecting a gene expression vector having an affinity tag inserted therein and cloning a target protein therein. Examples of vectors containing the affinity tag include, but are not limited to, pBIVT (Bioneer, Korea), pIVEX (Roche, Germany), pET (Novagen, Germany), pK7, pQE, etc.

In the present invention, when an affinity tag-free expression vector is selected, a nucleotide sequence expressing an affinity tag may be added to a template, and the affinity taq may be prepared by a gene recombination method.

As used herein, the term "cell lysate" refers to one prepared by high-pressure lysis after cell culture, and includes RNA polymerase required for mRNA and protein expression, cell constituents such as ribosomes, etc. The cells may be animal cells, microbial cells or plant cells. Preferably, the cells may be E. coli cells, but are not limited thereto.

In the method of the present invention, the "expression solution" is a supplement including amino acids required for transcription and translation, an energy source, buffer, etc. In the present invention, the term is used interchangeably with "protein expression solution". The expression solution is mixed with a template and a cell lysate and is used for protein synthesis.

As used herein, the term "small-molecule expression solution" means a solution containing triphosphate ribonucleic acid, amino acid and an energy source, which are required for cell-free protein expression, that is, transcription and translation. The term "protein expression mixture" means a solution which contains a cell lysate, an expression solution, buffer and the like and in which protein expression occurs. The term "template DNA" means an expression vector or PCR product that a promoter to be expressed, a terminator, and a protein-encoding nucleic acid sequence.

As used herein, the term "protease" means an enzyme having the ability to recognize and cleave a specific amino acid on a protein into amino acids or peptides. The term may be used interchangeably with endopeptidase.

In the method of the present invention, the protease is used to recognize an enzyme cleavage site inserted in a target protein and remove an affinity tag. Particularly, human rhinovirus 3C protease, TEV (Tobacco Etch Virus) protease, Factor Xa, Thrombin, bovine Enterokinase or the like, which can selectively recognize and cleave an enzyme cleavage site without cleaving a target protein, may be used. Preferably, TEV protease is used, but is not limited thereto.

As used herein, the term "enzyme cleavage site" refers to a specific amino acid sequence in a protein, which is recognized and cleaved by protease.

In the method of the present invention, the sequence of the enzyme cleavage site may vary depending on the kind of enzyme selected. For example, human rhinovirus 3C protease may be 'Leu-Glu-Val-Leu-Phe-Gln←Gly-Pro'; TEV (Tobacco Etch Virus) protease may be 'Glu-Asn-Leu-Tyr-Phe-Gln←Gly'; Factor Xa may be 'Ile-Glu-Gly-Arg←', Thrombin may be 'Leu-Val-Pro-Arg←Gly-Ser'; and bovine Enterokinase may be 'Asp-Asp-Asp-Asp-Lys←', but are not limited thereto (the symbol '←' is an enzyme cleavage site).

In the present invention, a method for synthesizing an affinity-tagged target protein may be an automated cell-free method for synthesizing an affinity-tagged protein, the method comprising the step of: (S10) adding a small-molecule expression solution to a mixture of a template, a cell lysate and a protein expression solution in a dialysis tube; (S20) maintaining the mixture in the reaction vessel to induce a protein synthesis reaction and promote protein expression; (S30) removing a small-molecule expression solution; (S40) mixing a magnetic bead suspension and a magnetic bead washing solution in a multi-well plate to equilibrate magnetic beads; (S50) moving the expressed protein product to the multi-well plate kit, and then adding the prepared magnetic beads thereto; (S60) applying a magnetic field to the unit well of step (S50), and removing a mixture of substances other than the magnetic bead-bound target protein; (S70) introducing a washing solution into the unit cell of step (S60), and removing the magnetic field to remove impurities other than the magnetic bead-bound target protein; (S80) applying a magnetic field while adding a protein elution buffer to obtain a solution containing the target protein separated from the magnetic beads; (S90) performing dialyzing by introducing the target protein-containing solution into a dialysis tube, and introducing a protein storage buffer into a protein dialysis unit; and (S100) removing the protein elution buffer.

Figure 9:
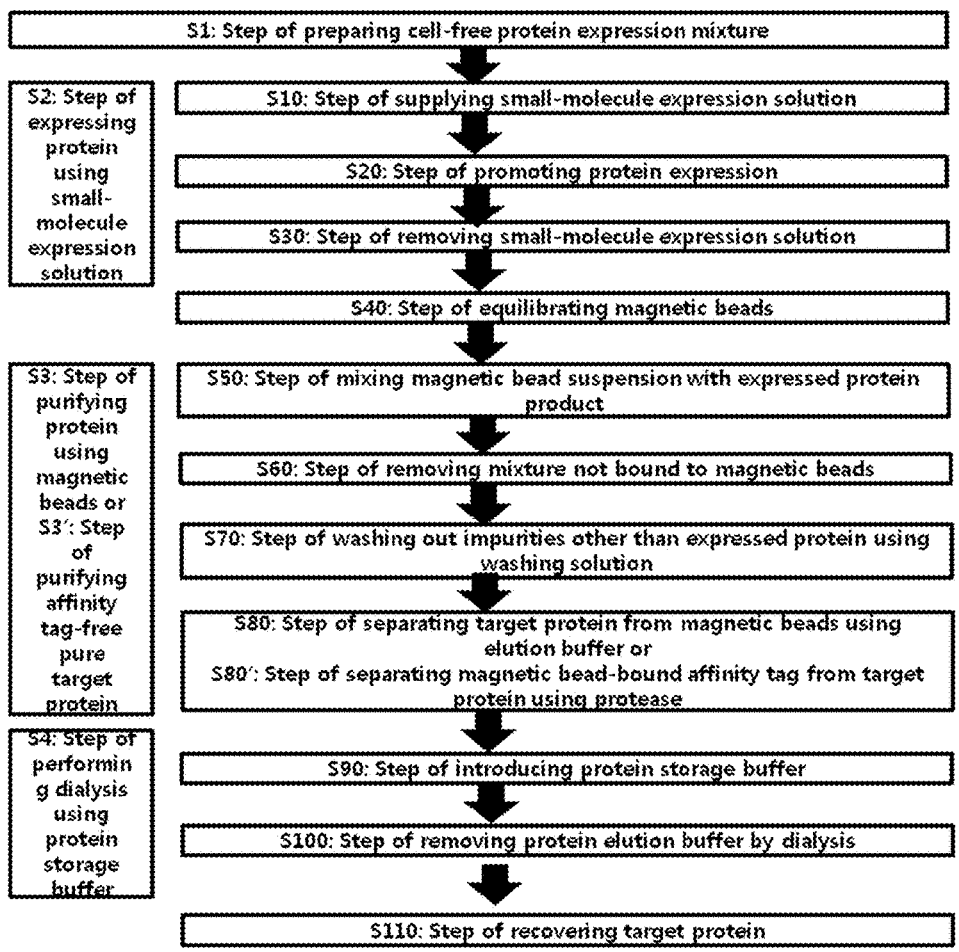
FIG. 9 is a flow chart of a method of producing a protein using an automated cell-free protein production system according to the present invention.

In the present invention, a method for synthesizing an affinity tag-free pure target protein may be an automated cell-free method for synthesizing an affinity tag-free protein, the method comprising the steps of: (S10) adding a small-molecule expression solution to a mixture of a template, a cell lysate and a protein expression solution in a dialysis tube; (S20) maintaining the mixture in the reaction vessel to induce a protein synthesis reaction and promote protein expression; (S30) removing a small-molecule expression solution; (S40) mixing a magnetic bead suspension and a magnetic bead washing solution in a multi-well plate to equilibrate magnetic beads; (S50) moving the expressed protein product to the multi-well plate, and then adding the prepared magnetic beads thereto; (S60) applying a magnetic field to the unit well of step (S50), and removing a mixture of substances other than the magnetic bead-bound target protein; (S70) introducing a washing solution into the unit cell of step (S60), and removing the magnetic field to remove impurities other than the magnetic bead-bound target protein; (S80') adding a protease reaction buffer to the unit well containing the magnetic bead-bound target protein to separate the magnetic bead-bound affinity tag from the target protein and bind the protease to the magnetic beads, thereby separating the target protein; (S90) performing dialysis by introducing the target protein-containing solution into a dialysis tube, and introducing a protein storage buffer into a protein dialysis unit; and (S100) removing the protein elution buffer (FIG. 9).

In an example of the present invention, a template DNA, a cell lysate, an expression solution, a small-molecule expression solution, an affinity tag removing TEV enzyme and a reaction solution, which are required for protein production, a magnetic bead suspension, a magnetic bead washing solution, a protein elution buffer and a protein storage buffer, were prepared. Using the automated cell-free protein production system of the present invention and the above samples, proteins were prepared.

In the preparation production method of the present invention, all the reactions excluding the step of preparing a cell-free protein expression mixture were automatically performed by the automated cell-free protein production system.

Figure 10:
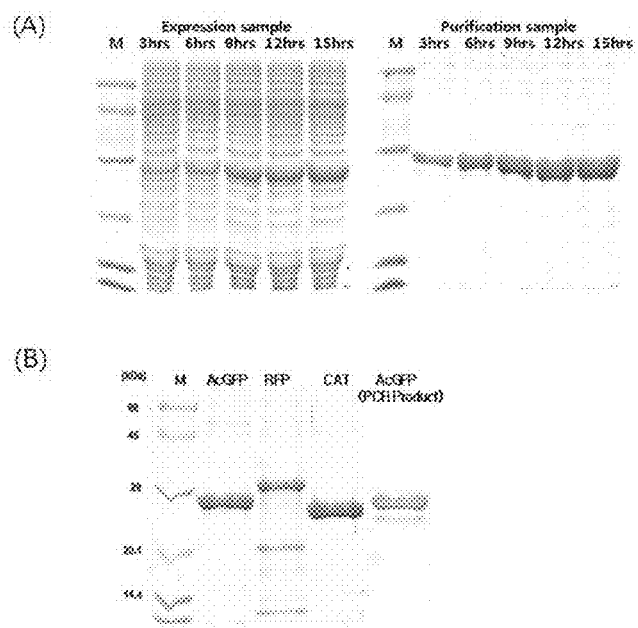
FIG. 10 shows the results of SDS-PAGE gel analysis of a target protein produced according to the present invention.

Using the automated cell-free protein production system of the present invention, AcGFP was prepared in six reaction wells while replacing a small-molecule expression solution in multiple steps. As shown in FIG. 10A, the prepared protein was analyzed on 12% SDS-PAGE gel, and as a result, it could be seen that the expression level of the protein increased as the small-molecule expression solution was sequentially replaced. In addition, it was shown that different proteins could be prepared using different templates (FIG. 10B).

Meanwhile, using the AcGFP gene containing a sequence, which is cleaved by TEV, as a template, a protein was prepared by a method of removing an affinity tag. As a result, as shown in FIG. 11, a sample purified by removing a histidine tag had a size smaller than that of the expressed sample, and was not detected by an antibody (Abcam) for the histidine tag.

EXAMPLES

Hereinafter, the present invention will be described in further detail with reference to examples. It will be obvious to a person having ordinary skill in the art that these examples are illustrative purposes only and are not to be construed to limit or change the scope of the present invention.

Example 1: Preparation of Template DNA 1-1: Preparation of Plasmid DNA

In the present invention, AcGFP, CAT, RFP and TEV-AcGFP genes were used for cell-free protein production. These genes were used to confirm whether protein was produced by the cell-free protein production system, and it will be obvious to those skilled in the art that the present invention may be applied to any proteins that are to be produced by cell-free protein production methods.

Each of the genes was synthesized by a gene synthesis method (*NBiochem. Biophys. Res. Commun.* 1998, 248, 200-203). Each of the synthesized genes was treated with a restriction enzyme, and then cloned into the histidine-tagged cell-free expression vector pBIVT (Bioneer, Korea). Meanwhile, TEV-AcGFP was constructed to include a sequence (Glu-Asn-Leu-Tyr-Phe-Gln←Gly), which is cleaved by TEV, between the histidine tag and the target protein.

Examples of an expression vector that may be used in the present invention include, but are not limited to, pBIVT (Bioneer, Korea), pIVEX (Roche, Germany), pET (Novagen, Germany), pK7, pQE, etc.

Specifically, restriction enzyme treatment and cloning were performed in the following manner.

For treatment of a synthesized gene product with a restriction enzyme, 1 μl of NdeI (Bioneer, Korea), 1 μl of SalI (Bioneer, Korea), 2 μl of 10× AccuCut™ buffer (Bioneer, Korea), 10 μl of a synthesized gene product and 6 μl of sterile distilled water were placed and mixed in each tube, and then incubated at 37° C. for 3 hours. For treatment of an expression vector with a restriction enzyme, 1 μl of NdeI (Bioneer, Korea), 1 μl of SalI (Bioneer, Korea), 2 μl of 10× AccuCut™ buffer (Bioneer, Korea), 10 μl of an expression vector and 6 μl of sterile distilled water were placed and mixed in each tube, and then incubated at 37° C. for 3 hours. From each of the reaction products treated with the restriction enzyme, DNA was purified using the Accuprep Gel Extraction kit (Bioneer, Korea).

Next, 5 μl of 2× rapid ligation buffer (Promega, USA), 1 μl of T4 DNA ligase (Promega, USA), 3 μl of the restriction enzyme-treated synthesized gene product and 1 μl of the restriction enzyme-treated vector were placed and mixed in each tube, and then incubated at 16° C. for 1 hours. Next, 10 μl of the incubated reaction solution was added to 100 μl of *E. coli* competent cells, and kept on ice for 30 minutes, and then incubated at 42° C. for 90 seconds, and kept on ice for 5 minutes. The reaction solution was seeded on a kanamycin-containing LB plate, and then incubated at 37° C. for 16 hours.

The white colony was collected, and incubated in 10 µl of LB liquid medium for about 16 hours, after the solution was centrifuged to remove the supernatant, and plasmid DNA was purified from the pellet using an AccuPrep plasmid DNA prep kit (Bioneer, Korea). The purified DNA was sequenced to confirm whether the gene synthesized by each gene synthesis method was correct. To obtain DNA to be used for protein synthesis, the corresponding colony was incubated, and plasmid DNA was purified in the same manner as described above. The plasmid DNA had a purity ($A_{260/280}$) of 1.8-2.0 as measured by a UV spectrophotometer (Shimazu, Japan).

1-2: Preparation of PCR Product

To construct a PCR product, ExiProgen™ ProXpress PCR Template Kit (Bioneer, Korea) was used.

Specifically, for amplification of a target gene, a set of primers having an overlapping sequence at the 5' and 3' terminal ends were prepared, and primary PCR was performed using a sample (genomic DNA, T vector, etc.) having the target gene as a template. In the PCR reaction, AccuPower ProFi Taq PCR Premix provided in the kit was used. The PCR reaction conditions were as follows: initial denaturation at 94° C. for 5 min, and then 30 cycles, each consisting of 94° C. for 30 sec, 58° C. for 30 sec and 72° C. for 1 min, followed by final extension at 72° C. for 5 min. The primary PCR product was purified using an AccuPrep Gel Extraction kit (Bioneer, Korea).

Using the primary PCR product as a template, secondary overlapping PCR was performed to synthesize a PCR fragment for protein synthesis. The PCR reaction was performed by adding the cassette set and primer set provided in the kit, and the PCR reaction conditions were as follows: denaturation at 94° C. for 5, and then 30 cycles, each consisting of 94° C. for 1 min, 48° C. for 1 min and 72° C. for 1 min, followed by final extension at 72° C. for 5 min. The secondary PCR product was purified using the AccuPrep Gel Extraction kit (Bioneer, Korea).

Example 2: Preparation of Cell Lysate

First, E. coli cells (BL21(DE3); Novagen, USA) were cultured in a 350 l fermenter (2×YT medium) at 37° C. At an absorbance ($OD_{600}$) of 0.6, 1 mM IPTG was added to express T7 RNA polymerase, and at an absorbance ($OD_{600}$) of 3.0-3.5, the culture was stopped, and the cells were harvested by centrifugation and stored at −50° C.

100 g of the harvested E. coli cells were washed with 500 ml of a washing buffer (10 mM Tris(oAc) pH 8.2, 14 mM Mg(oAc)$_2$, mM K(OAc), 1 mM DTT (dithiothreitol), 0.05% (v/v) 2-mercaptoethanol (2-ME)), and then centrifuged (at 3,000 RPM for 30 min). This procedure was repeated 4 times.

After washing, the E. coli cells were weighed, and added to and dispersed in a buffer (10 mM Tris(oAc) pH 8.2, 14 mM Mg(oAc)2, 60 mM K(OAc), 1 mM DTT (dithiothreitol)) having a volume corresponding to 1.1 times the weight thereof. Then, the cells were lysed using a cell homogenizer (Pressure Cell Homogeniser, Stansted Fluid Power) under a pressure of constant pressure (280 psi).

The cell lysate was centrifuged at 16,000 RPM at 4° C. for minutes, and the supernatant was collected. Then, a buffer (10 mM Tris(oAc) pH 8.2, 14 mM Mg(oAc)2, 60 mM K(OAc), 1 mM DTT (dithiothreitol)) was added to the supernatant in an amount of 3 µl per 10 µl of the cell lysate, and 26.7 g/ml creatine kinase was added thereto. Then, the solution was incubated at 37° C. for 80 minutes, thereby obtaining a precultured solution. Next, the pre-cultured solution was centrifuged (11,000 RPM, 20 min, 4° C.), thereby obtaining a cell lysate. The cell lysate was stored at −70° C. until use.

Example 3: Preparation of Expression Solution and Small-Molecule Expression Solution An expression solution to be added for cell-free protein expression was prepared by mixing 114 mM HEPES-KOH (pH 7.5), 2.4 mM ATP, each 1.7 mM CTP, GTP and UTP, 2 mM DTT, 90 mM K(Glu), 80 mM NH$_4$(OAc), 12 mM Mg(OAc), 68 g/ml folinic acid (L-5-formyl-5,6,7,8-tetrahydrofolic acid), 2.5 mM amino acids mixture, 2% PEG 8000 and 67 mM creatine phosphate with one another. In addition, a small-molecule expression solution was prepared by mixing the expression solution, DEPC DW and 5% NaN$_3$ at a ratio of 46.7:52.3:1.

The expression solution and the small-molecule expression solution were stored at −20° C. until use.

Example 4: Preparation of Affinity Tag Removing TEV Enzyme and Reaction Solution 4-1: Preparation of Expression Vector and Construction of Strain TEV gene was prepared by synthesizing a gene optimized for E. coli codon. The gene synthesized by the gene synthesis method (Lo-Chun Au et al., *Biochem. Biophys. Res. Commun.*, 248(1):200, 1998) contained a histidine tag-encoding sequence upstream of TEV enzyme. 10 µl of the synthesized gene, 1 µl of Nde I (Bioneer, Korea), 1 µl of XhoI (Bioneer, Korea), 2 µl of 10× AccuCut™ buffer (Bioneer, Kores), and 6 µl of sterile distilled water were placed and mixed in each tube, and then incubated at 37° C. for 3 hours, thereby obtaining a gene fragment. Meanwhile, using the same enzyme and conditions as above, pCold (TaKaRa, Japan) was treated. Each DNA was purified using an Accuprep Gel Extraction kit (Bioneer, Korea).

3 µl of the purified TEV gene fragment and 1 µl of the vector were mixed with 5 µl of 2× rapid ligation buffer (Promega, USA) and 1 µl of T4 DNA ligase (Promega, USA), and then ligated with each other at 16° C. for 1 hour.

Next, 10 µl of the ligation product was added to 100 µl of DH-5a competent cells, kept on ice for 30 minutes, incubated at 42° C. for 90 seconds, and then kept on ice for 5 minutes, so that the ligated vector would be inserted into the cells. Next, the cells were seeded on 100 µg/ml ampicillin-containing LB plate, and statically cultured at 37° C. for 16 hours.

The cultured white colony was collected, shake-cultured in 10 µl of ampicillin-containing LB liquid medium for 16 hours, and then centrifuged. The supernatant was removed, and the expression vector pCold-TEV having the TEV gene inserted therein was purified from the pellet using an Accu-Prep plasmid DNA prep kit (Bioneer, Korea).

1 µl of the above-prepared pCold-TEV expression vector was added to 100 µl of BL21(DE3) competent cells. Then, the cells were kept on ice for 30 minutes, incubated at 42° C. for 90 seconds, and then kept on ice for 5 minutes, so that the expression vector would be inserted into the cells. Then, the cells were seeded on 100 µg/ml ampicillin-containing LB plate, and statically cultured at 37° C. for 16 hours, thereby obtaining an expression strain.

4-2: Cell Culture

The TEV expression strain obtained as described above was cultured in LB medium in the order of 3 ml, 100 ml and 2 l at a temperature of 37° C., thereby obtaining a seed. The prepared seed was added to 70 l of LB medium, and then cultured at a temperature of 37° C. At an absorbance ($OD_{600}$) of 0.4, 0.1 mM IPTG was added to the cells, which were then cultured at a temperature of 18° C. for 16 hours. Next, the cells were recovered by centrifugation.

4-3: Purification of TEV Enzyme 100 g of the bacterial cells were added and suspended uniformly in 1000 µl of cell lysis buffer (20 mM Tris HCl (pH 8.0), 1 mM PMSF (Phenylmthyl Sulfonyl Fluoride), 1 mM 2-mercaptoethanol (2-ME)), and then lysed using a cell homogenizer (Pressure Cell Homogeniser, Stansted Fluid Power) under a constant pressure (280 psi).

The cell lysate was centrifuged (11,000 RPM, 30 min, 4° C.). The supernatant was added to 40% 5% of streptomycin sulfate, and then centrifuged (11,000 RPM, 15 min, 4° C.) to remove nucleic acid.

Ammonium sulfate was added in an amount corresponding to 0.314 times the volume of the collected cell lysate, followed by centrifugation (11,000 RPM, 15 min, 4° C.), and the pellet was collected. The pellet was suspended in 200 µl Ni column buffer (50 mM $NaH_2PO_4$ pH 8.0, 300 mM NaCl, 10 mM Imidazole), and then added to a dialysis tube (10 kDa, Dialysis Tubing, Sigma, USA) and dialyzed (12 hr, 4° C.) with a 50-fold volume of Ni column buffer to remove impurities. The solution in the dialysis tube was centrifuged (11,000 RPM, 20 min, 4° C.), and the supernatant was collected, and then added to a column packed with Ni-agarose resin (GE Healthcare). Next, a protein-containing eluate was collected using Ni column elution buffer (50 mM $NaH_2PO_4$ pH 8.0, 300 mM NaCl, 500 mM imidazole).

The protein eluate was added to the same tube as described above, was dialyzed (12 hr, 4° C.) with a 100-fold volume of DEAE column buffer (20 mM Tris HCl pH8.0, 50 mM KCl, 0.5 mM EDTA, 1 mM 2-mercaptoethanol(2-ME)), followed by centrifugation (11,000 RPM, 20 min, 4° C.) and the supernatant was collected. The supernatant was run through a column packed with DEAE resin (GE Healthcare). Because the TEV protein does not bind to DEAE resin, the solution not bound to the resin was collected, added to a dialysis tube (10 kDa, Dialysis Tubing, Sigma, USA), and dialyzed with a 50-fold volume of TEV storage buffer (50 mM Tris HCl pH 7.6, 1 mM EDTA, 1% Trinton X-100, 50% glycerol), followed by concentration. The finally collected TEV enzyme was stored at −20° C. until use.

4-4: Preparation of Solution for Reaction of TEV Enzyme

A solution (50 mM HEPES-KOH (pH7.5), 100 mM NaCl, 10 mM imidazole, 5 mM 2-mercaptoethanol (2-ME), 0.5 mM EDTA, 1 mM DTT and 10% (v/v) glycerol) for the reaction of the TEV enzyme was prepared. The solution to be used to remove an affinity tag from a target protein was stored at −20° C. until use.

Example 5: Preparation of Magnetic Bead Suspension and Washing Solution 5-1: Preparation of Magnetic Bead Suspension Magnetic beads to be used for protein purification were magnetic iron (Fe) particles, coated with silica and complexed with nickel (Ni) at the end. As magnetic beads, Ni-NTA silica magnetic beads (Bioneer, Korea) were used. A magnetic bead suspension was prepared by suspending magnetic beads in 20% ethanol to prepare 10% slurry.

5-2: Preparation of Magnetic Bead Washing Solution

Washing solutions required for protein purification was prepared. Specifically, magnetic particle washing solution I (50 mM HEPES-KOH, 300 mM NaCl, 10 mM Imidazole, 5 mM 2-mercaptoethanol(2-ME), and 10% (v/v) glycerol) was prepared.

Meanwhile, for removal of an affinity tag, magnetic particle washing solution II (50 mM HEPES-KOH, 100 mM NaCl, mM imidazole, 5 mM 2-mercaptoethanol(2-ME), 0.5 mM EDTA, 1 mM DTT, and 10% (v/v) glycerol) was prepared and used.

The magnetic particle washing solutions were used at 4° C. until use.

Example 6: Preparation of Protein Elution Buffer and Protein Storage Buffer 6-1: Preparation of Protein Elution Buffer A protein elution buffer required for protein purification was prepared. Specifically, a protein elution buffer (50 mM HEPES-KOH, 300 mM NaCl, 1 M imidazole, 5 mM 2-mercaptoethanol (2-ME), and 10% (v/v) glycerol) was prepared. This solution was stored at 4° C. until use.

6-2: Preparation of Protein Storage Buffer

After purification of the target protein, a protein storage buffer for storing the protein was prepared. Specifically, a protein storage buffer (50 mM Tris-Cl (pH7.6), 100 mM NaCl, 1 mM DTT, 0.1 mM EDTA, 0.05% (v/v) NaN3, and 50% (v/v) glycerol) was used. This solution was stored at 4° C. until use.

Example 7: Production of Protein Using Automated Cell-Free Protein Production System (1) Step of Preparing Cell-Free Protein Expression Mixture A mixture for cell-free protein expression was prepared in the same manner.

Dialysis tubes, the inside and outside of which were washed with sterile distilled water, were inserted into the dialysis tube holes of the reaction vessels in a protein expression reaction unit and a protein dialysis unit, and then each dialysis tube of the protein dialysis unit was filled with 0.5 µl of sterile distilled water.

Next, the template DNA, cell lysate and expression solution were dissolved at room temperature, and introduced and mixed in the dialysis tubes of the protein expression reaction unit.

(2) Step of Expressing Protein Using Small-Molecule Expression Solution

A small-molecule expression solution can be supplied to a multi-well plate kit or a solution container, and an expression method may be changed according to the amount of samples as follows.

A. 24 Kinds or Less of Samples

Protein expression is performed using the first or second reaction vessel shown in FIG. 3 or 4 while a small-molecule expression solution is supplied to the multi-well plate kit.

A pipette introduces the small-molecule expression solution of the multi-well plate kit into the small-molecule expression solution hole of the reaction vessel of the protein expression reaction unit. Herein, the volume of small-molecule expression solution hole corresponds to about 2.5-3 times the volume of each protein expression mixture. The reaction temperature control unit located under the protein expression reaction unit is heated (26~38° C.), and a pipette is inserted into the small-molecule expression solution hole to periodically mix the solution. In this process, an energy source and the like in the small-molecule expression solution are introduced into the mixture through the dialysis membrane of the dialysis tube containing the protein expression mixture, and protein expression inhibitors in the mixture are discharged from the dialysis membrane to promote protein expression. After 3 hours, the pipette sucks the small-molecule expression solution from the small-molecule expression solution hole and discards the sucked solution into the waste container, and then a fresh small-molecule expression solution supplied from the multi-well plate kit is introduced into the small-molecule expression solution hole of the reaction vessel. This process of replacing the small-molecule expression solution in multiple steps may be repeated 5-6 times.

B. 24 Kinds or More of Samples

Protein expression is performed using the third or fourth reaction vessel shown in FIG. 5 or 6 while the small-molecule expression solution is supplied to the solution container.

The small-molecule expression solution is supplied from the solution container into the small-molecule expression solution container through the inlet connected to the reaction vessel. Herein, the volume of the small-molecule expression solution corresponds to 10-20 times the volume of the protein expression mixture. The reaction temperature control unit located under the protein expression reaction unit is heated at (26~38° C.) for about 16-20 hours. The energy source and the like in the protein expression mixture are introduced into the mixture through the dialysis membrane of the dialysis tube, and protein expression inhibitors in the mixture are discharged from the dialysis membrane to promote protein expression.

After the completion of protein expression, the small-molecule expression solution is discarded into the waste container through the outlet. This step of introducing and removing the small-molecule expression solution may be repeated once or more.

(3) Step of Purifying Protein Using Magnetic Beads

The magnetic bead suspension, magnetic bead washing solution and protein elution buffer required for protein purification are supplied to the multi-well plate kit.

A. Purification of Affinity-Tagged Target Protein

The pipette moves the magnetic bead suspension of the multi-well plate kit to the multi-well plate kit of the protein purification unit, and then mixes the suspension with the magnetic bead washing solution. The magnetic particles are attached to the wall side of the multi-well plate kit by the magnetic field application device of the protein purification unit, and then the magnetic bead washing solution is removed.

Using the pipettes, the protein expression mixture in the dialysis tube is moved to the multi-well plate kit containing the magnetic particles, and then mixed with the magnetic particles. In this process, the histidine-tagged target protein binds divalent ions on the magnetic bead surface. The target protein-bound magnetic beads are attached to the wall side of the multi-well plate kit by the magnetic field application device, and then impurities are removed therefrom.

The magnetic particle washing solution is introduced into the well containing the target protein-bound magnetic beads, and then mixed using the pipette to suspend the magnetic beads. In this process, a histidine tag-free protein bound to the magnetic beads is separated from the magnetic beads. Then, the magnetic particles are attached to the wall side of the multi-well plate kit by the magnetic field application device, and then the washing solution containing impurities is removed. This process may be repeated 6-8 times.

After completion of the washing, the protein elution buffer is introduced into the well containing the target protein-bound magnetic beads, and then mixed using the pipette. In this process, the target protein is separated from the magnetic beads into the solution. The magnetic beads are attached to the wall side of the multi-well plate kit by the magnetic field application device, and then the eluted target protein solution is recovered. The recovered solution is moved into the dialysis tube located in the protein dialysis unit.

B. Purification of Affinity Tag-Free Pure Target Protein

The pipette moves the magnetic bead suspension of the multi-well plate kit to the multi-well plate kit of the protein purification unit, and then mixed the suspension with the magnetic bead washing solution. The magnetic beads are attached to the wall side of the multi-well plate kit by the magnetic field application device of the protein purification unit, and then the magnetic bead washing solution is removed.

Using the pipette, the protein expression mixture in the dialysis tube is moved to the multi-well plate kit containing the magnetic beads, and then mixed with the magnetic beads. in this process, a histidine-tagged target protein binds to divalent ions on the magnetic bead surface. The target protein-bound magnetic beads are attached to the wall side of the multi-well plate kit by the magnetic field application device, and then impurities are removed.

The magnetic bead washing solution is introduced into the well containing the target protein-bound magnetic beads, and then mixed using the pipette to suspend the magnetic beads. In this process, a histidine tag-free protein is detached from the magnetic beads. Next, the magnetic beads are attached to the wall side of the multi-well plate kit by the magnetic field application device, and then the washing solution containing impurities is removed. This process may be repeated 6-8 times.

After completion of the washing, the TEV enzyme/reaction solution mixture is introduced into a well containing the target protein-bound magnetic beads, and then mixed using the pipette. The well is heated at 30° C. for 1 hour by the reaction temperature control unit located under the protein purification unit. In this process, the target protein is separated from the affinity tag, and thus is separated from the magnetic beads into the solution. The solution contains the affinity tag-free target protein together with the TEV enzyme. The magnetic beads are attached to the side wall of the multi-well plate kit by the magnetic field application device, and then the solution containing the target protein is bound to fresh magnetic beads. In this process, the histidine-tagged TEV enzyme binds to the magnetic beads, and the target protein is present in the supernatant without being bound to the magnetic beads.

Next, the TEV enzyme-bound magnetic beads are attached to the wall side of the multi-well plate kit by the magnetic field application device, and then the final target protein solution is recovered and moved into the dialysis tube located in the protein dialysis unit.

(4) Step of Dialysis Using Protein Storage Buffer

The protein storage buffer may be supplied to the multi-well plate kit or the solution container, and an expression method may be changed according to the number of samples as follows.

A. 24 Kinds or Less of Samples

Dialysis is performed using the first or second reaction vessel shown in FIG. 3 or 4 while the protein storage buffer is supplied to the multi-well plate kit.

The pipette introduces the protein storage buffer of the multi-well plate kit into the dialysis solution hole of the reaction vessel located in the protein dialysis unit. Herein, the volume of the buffer corresponds to about 2 times the volume of each target protein solution. The reaction temperature control unit located under the protein dialysis unit is cooled (4~8° C.), and the pipette periodically mixes the solution in the dialysis solution hole. In this process, the protein elution buffer contained in the target protein solution is replaced with the protein storage buffer through the dialysis membrane of the dialysis tube. After 3 hours, the pipette sucks the protein storage buffer from the dialysis hole and discards the buffer into the waste container, and then a fresh protein storage buffer supplied from the multi-well plate kit is introduced into the dialysis solution hole of the reaction vessel. This step of replacing the protein storage buffer in multiple steps may be repeated 5-6 times.

B. 24 Kinds or More of Samples

Dialysis is performed using the third or fourth reaction vessel shown in FIG. 5 or 6 while the protein storage buffer is supplied to the solution container.

The protein storage buffer is introduced from the solution container into the dialysis vessel through the inlet connected to the reaction vessel. Herein, the volume of the protein storage buffer corresponds to 10-20 times the volume of the target protein solution. The reaction temperature control unit located under the protein dialysis unit is cooled (4~8° C.) for about 16-20 hours. In this process, the protein elution buffer contained in the target protein solution is replaced with the protein storage buffer through the dialysis membrane of the dialysis tube. This step of replacing protein elution buffer with the protein storage buffer in multiple times may be repeated once or more.

Example 8: Analysis of Expression Level of Protein Produced by Automated Cell-Free Protein Production System The expression level of the protein produced using the automated cell-free protein production system according to the method of Example 7 was analyzed by SDS-PAGE and Western blotting.

Using the automated cell-free protein production system of the present invention, AcGFP was produced in 6 wells while the small-molecule expression solution was replaced in multiple steps. As a result, as can be seen in FIG. 10A showing the results of 12% SDS-PAGE gel analysis, the expression level of the protein increased as the small-molecule expression solution was replaced in multiple steps.

In addition to AcGFP, other proteins such as CAT, RFP and AcGFP (PCR product) could be produced (FIG. 10B).

Meanwhile, the protein was produced by the method of removing the affinity tag while using the AcGFP gene containing a sequence, which is cleaved by TEV, as a template. As a result, as shown in FIG. 11A, the size of the histidine tag-free purified sample (P) was smaller than that of the expressed sample (E). Also, Western blotting was performed using histidine tag antibody (Abcam), and as a result, it was shown that a histidine tag-free purified sample was not detected (FIG. 11B).

INDUSTRIAL APPLICABILITY

The automated cell-free protein production system according to the present invention has advantages in that it can automatically express and purify a target protein, and the finally produced protein can be immediately used because it can be dialyzed against a protein storage buffer.

In the protein production method according to the present invention, an energy source and the like, required for protein expression, can be continuously supplied by replacing the small-molecule expression solution in multiple steps, a target protein can be produced in an amount up to five times that obtained by a conventional batch-type cell-free protein production method. In addition, a pure target protein can be produced by removing the unnecessary affinity tag using protease, during the purification of the target protein using magnetic beads. Thus, according to the present invention, in the production of proteins for industrial, medical and research purposes, it is possible to produce pure proteins free of an artificial sequence that can adversely affect the activity and structure of proteins.

Although the present invention has been described in detail with reference to the specific features, it will be apparent to those skilled in the art that this description is only for an embodiment and does not limit the scope of the present invention. Thus, the substantial scope of the present invention will be defined by the appended claims and equivalents thereof.

The invention claimed is:

1. An automated cell-free protein production system comprising:
   a protein expression reaction unit comprising a reaction vessel that includes one or more dialysis tubes, each including a cylindrical dialysis membrane extending between a top portion and a bottom portion of the dialysis tube and forming a circumscribing side wall of the dialysis tube and being open at its top end;
   a reaction temperature control unit configured to heat or cool the reaction vessel;
   a pipette array comprising one or more pipettes and configured to suck or discharge solutions using the pipettes;
   a pipette array moving unit configured to move the pipette array in an upward and downward direction, a forward and backward direction or a left and right direction so as to move solutions;
   a protein purification unit including a magnetic field application device; and
   a multi-well plate mounting unit having mounted therein a multi-well plate kit configured to supply solutions that are used for protein production,
   wherein the reaction vessel of the protein expression reaction unit is of unitary block form, and comprises an array of hole pairs at a top face of the reaction vessel, each hole pair open at said top face and extending interiorly into the reaction vessel of unitary block form, comprising a cylindrical dialysis tube hole configured to receive one of the dialysis tubes, and a cylindrical small molecule expression solution hole, wherein the dialysis tube hole and the small molecule expression solution hole in each hole pair are transversely spaced apart from one another and are interconnected in fluid communication with one another by a transversely extending channel therebetween, wherein the small molecule expression solution is automatically and continually supplied to the small molecule expression solution hole in each hole pair whose dialysis tube hole contains a dialysis tube, and wherein the pipette array is automatically and periodically translated by the pipette array moving unit to insert pipettes of the pipette array into respective small molecule expression solution holes containing small molecule expression solution, to mix the solution therein that is in fluid communication with the cylindrical dialysis membranes of the dialysis tubes in the dialysis tube holes in the array of hole pairs in the protein expression reaction unit.

2. The automated cell-free protein production system of claim 1, wherein the reaction vessel comprises 16, 48, or 96 cylindrical dialysis tube holes for receiving said dialysis tubes.

3. The automated cell-free protein production system of claim 1, wherein the reaction vessel further comprises a reaction vessel cover configured to cover the reaction vessel to prevent evaporation of solution from the dialysis tubes, the reaction vessel cover having one or more incisions that allow the pipettes to be inserted into the dialysis tubes.

4. The automated cell-free protein production system of claim 1, wherein the protein expression reaction unit further comprises a protein dialysis unit including: one or more dialysis tube holes formed in the top thereof and configured to receive the dialysis tubes; and one or more dialysis solution holes formed adjacent to the dialysis tube holes so as to fluidically communicate with the dialysis tube holes and configured to receive a protein storage buffer.

5. The automated cell-free protein production system of claim 1, wherein the protein expression reaction unit comprises:
an openable/closable outlet configured to allow a solution to be discharged from the reaction vessel therethrough;
a waste container connected to the outlet so as to fluidically communicate with the outlet;
an inlet configured to allow a solution to be introduced into the reaction vessel therethrough;
a metering pump configured to supply a solution into the inlet; and
one or more solution containers connected to the metering pump.

6. The automated cell-free protein production system of claim 5, wherein the protein expression reaction unit further comprises a multi-channel valve configured such that one side thereof is connected with the metering pump and the other side thereof fluidically communicates with any one selected from among the solution containers.

7. The automated cell-free protein production system of claim 1, wherein the protein expression reaction unit comprises:
a solution passage configured to allow a solution to be supplied or discharged to or from the reaction vessel therethrough;
a bidirectional metering pump connected with the solution passage and configured to supply or discharge a solution to or from the reaction vessel;
one or more solution containers connected with the bidirectional metering pump;
one or more waste containers connected with the bidirectional metering pump; and
a multi-channel valve configured such that one side thereof is connected with the bidirectional metering pump and the other side thereof is connected with the solution containers and the waste containers, so that any one selected from among the solution containers or the waste containers fluidically communicate with the bidirectional metering pump through the multi-channel valve.

8. The automated cell-free protein production system of claim 1, wherein the pipette array comprises 1 to 96 pipettes arranged according to the size of the reaction vessel and the number of the pipettes in such a manner as to be automatically attached or detached thereto or therefrom and is configured to suck and discharge a desired amount of a solution.

9. The automated cell-free protein production system of claim 1, wherein the multi-well plate kit mounted in the multi-well plate mounting unit comprises individual separate unit wells for storing a solution required for cell-free protein production.

10. The automated cell-free protein production system of claim 9, wherein the multi-well plate kit is dispensed with one or more solutions required for cell-free protein production selected from the group consisting of a protein storage buffer, a sterile distilled water, a magnetic bead suspension, a magnetic bead washing solution, a protein elution buffer, a small-molecule expression solution, a protease reaction buffer, and a solution for membrane protein synthesis.

11. The automated cell-free protein production system of claim 1, wherein the reaction temperature control unit and the magnetic field application device are constructed so as to be simultaneously controlled at the same position.

12. An automated cell-free protein production method comprising the steps of:
(a) preparing a cell-free protein expression mixture (SI);
(b) expressing a protein using a small-molecule expression solution (S2);
(c) purifying the protein using magnetic beads (S3); and
(d) dialyzing the purified protein using a protein storage buffer (S4),
wherein step (b) of expressing the protein comprises the steps of: (i) introducing a small-molecule expression solution; (ii) promoting the expression of a protein; and (iii) removing the small-molecule expression solution therefrom are sequentially repeated one or more times,
wherein the automated cell-free protein production method is conducted in the automated cell-free protein production system of claim 1.

13. The automated cell-free protein production method of claim 12, wherein step (c) of purifying a protein using magnetic beads comprising a step of, once or more, sequentially repeating the steps of (i) introducing a magnetic bead washing solution; and (ii) applying/removing a magnetic field so as to remove impurities from the magnetic bead.

14. The automated cell-free protein production method of claim 12, wherein step (c) of purifying a protein using magnetic beads comprises a step of isolating a target protein from the magnetic bead by introducing a protein elution buffer.

15. The automated cell-free protein production method of claim 12, wherein the magnetic beads are magnetic beads having bound thereto divalent metal ions.

16. The automated cell-free protein production method of claim 12, wherein step (d) of dialyzing the purified protein using the protein storage buffer comprise a step of, once or more, sequentially repeating the steps of: (i) supplying the protein storage buffer into a dialysis solution hole; and (ii) removing the protein elution buffer from the dialysis tube.

17. The automated cell-free protein production method of claim 12, wherein step (c) of purifying the protein using a magnetic bead (S3) is step (c') of purifying an affinity tag-free pure target protein (S3').

18. The automated cell-free protein production method of claim 17, wherein step (c') of purifying an affinity tag-free pure target protein (S3') comprises the steps of:
a step of removing affinity tag, which isolates the affinity tag from the target protein by treatment with an enzyme that recognizes an enzyme cleavage site and an enzyme reaction solution; and removing a protease.

19. The automated cell-free protein production method of claim 17, wherein the affinity tag is histidine or cysteine.

20. The automated cell-free protein production method of claim 18, wherein the protease is selected from the group consisting of TEV (Tobacco Etch Virus) protease, Factor Xa, Thrombin, bovine Enterokinase, and human rhinovirus 3C protease.

* * * * *